(12) United States Patent
Garcia et al.

(10) Patent No.: US 8,382,825 B2
(45) Date of Patent: Feb. 26, 2013

(54) FLEXIBLE VASCULAR OCCLUDING DEVICE

(75) Inventors: Adrian Garcia, Los Gatos, CA (US); Ting Tina Ye, San Jose, CA (US); Quang Q Tran, Redwood City, CA (US); Aaron L Berez, Menlo Park, CA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/045,491

(22) Filed: Mar. 10, 2011

(65) Prior Publication Data

US 2011/0166592 A1    Jul. 7, 2011

Related U.S. Application Data

(60) Division of application No. 11/420,025, filed on May 24, 2006, now abandoned, which is a continuation-in-part of application No. 11/136,395, filed on May 25, 2005.

(60) Provisional application No. 60/574,429, filed on May 25, 2004.

(51) Int. Cl.
*A61F 2/06* (2006.01)
(52) U.S. Cl. ............ 623/1.53; 623/1.15; 623/1.51
(58) Field of Classification Search ............... 623/1.53, 623/1.1–1.16
See application file for complete search history.

(56) References Cited

U.S. PATENT DOCUMENTS

| | | | |
|---|---|---|---|
| 2,919,467 A * | 1/1960 | Mercer .................. | 264/167 |
| 4,321,711 A | 3/1982 | Mano | |
| 4,503,569 A | 3/1985 | Dotter | |
| 4,512,338 A | 4/1985 | Balko et al. | |
| 4,538,622 A | 9/1985 | Samson et al. | |
| 4,580,568 A | 4/1986 | Gianturco | |
| 4,655,771 A | 4/1987 | Wallsten | |
| 4,733,665 A | 3/1988 | Palmaz | |
| 4,743,251 A | 5/1988 | Barra | |
| 4,768,507 A | 9/1988 | Fischell et al. | |
| 4,776,337 A | 10/1988 | Palmaz | |
| 4,954,126 A | 9/1990 | Wallsten | |
| 5,011,488 A | 4/1991 | Ginsburg | |
| 5,035,706 A | 7/1991 | Giantureo et al. | |
| 5,061,275 A | 10/1991 | Wallsten et al. | |
| 5,108,416 A | 4/1992 | Ryan et al. | |
| 5,160,341 A | 11/1992 | Brenneman et al. | |
| 5,180,368 A | 1/1993 | Garrison | |

(Continued)

FOREIGN PATENT DOCUMENTS

| CN | 101472537 A | 7/2009 |
|---|---|---|
| FR | 2556210 B1 | 4/1988 |

(Continued)

OTHER PUBLICATIONS

Benndorf, et al. Treatment of a Ruptured Dissecting Vertebral Artery Aneurysm with Double Stent Placement: Case Report AJNR Am J Neuroradiol, Nov.-Dec. 2001, vol. 22, pp. 1844-1848.

(Continued)

*Primary Examiner* — Thomas J Sweet
*Assistant Examiner* — Christopher D Prone
(74) *Attorney, Agent, or Firm* — Mark J. Kertz, Esq.

(57) ABSTRACT

A vascular occluding device for modifying blood flow in a vessel, while maintaining blood flow to the surrounding tissue. The occluding device includes a flexible, easily compressible and bendable occluding device that is particularly suited for treating aneurysms in the brain. The neurovascular occluding device can be deployed using a micro-catheter. The occluding device can be formed by braiding wires in a helical fashion and can have varying lattice densities along the length of the occluding device. The occluding device could also have different lattice densities for surfaces on the same radial plane.

12 Claims, 22 Drawing Sheets

U.S. PATENT DOCUMENTS

| | | | |
|---|---|---|---|
| 5,192,297 A | 3/1993 | Hull | |
| 5,201,757 A | 4/1993 | Heyn et al. | |
| 5,209,731 A | 5/1993 | Sterman et al. | |
| 5,242,399 A | 9/1993 | Lau et al. | |
| 5,246,420 A | 9/1993 | Kraus et al. | |
| 5,246,445 A | 9/1993 | Yachia et al. | |
| 5,344,426 A | 9/1994 | Lau et al. | |
| 5,360,443 A | 11/1994 | Barone et al. | |
| 5,382,259 A | 1/1995 | Phelps et al. | |
| 5,401,257 A | 3/1995 | Chevalier, Jr. et al. | |
| 5,405,380 A | 4/1995 | Gianotti et al. | |
| 5,415,637 A | 5/1995 | Khosravi | |
| 5,421,826 A | 6/1995 | Crocker et al. | |
| 5,423,849 A | 6/1995 | Engelson et al. | |
| 5,449,372 A | 9/1995 | Schmaltz et al. | |
| 5,458,615 A | 10/1995 | Klemm et al. | |
| 5,476,505 A | 12/1995 | Limon | |
| 5,480,423 A | 1/1996 | Ravenscroft et al. | |
| 5,484,444 A | 1/1996 | Braunschweiler et al. | |
| 5,489,295 A | 2/1996 | Piplani et al. | |
| 5,507,768 A | 4/1996 | Lau et al. | |
| 5,522,822 A | 6/1996 | Phelps et al. | |
| 5,534,007 A | 7/1996 | St. Germain et al. | |
| 5,546,880 A * | 8/1996 | Ronyak et al. | 112/475.01 |
| 5,562,641 A | 10/1996 | Flomenblit et al. | |
| 5,562,728 A | 10/1996 | Lazarus et al. | |
| 5,591,225 A | 1/1997 | Okuda | |
| 5,599,291 A | 2/1997 | Balbierz et al. | |
| 5,607,466 A | 3/1997 | Imbert et al. | |
| 5,609,625 A | 3/1997 | Piplani et al. | |
| 5,626,602 A | 5/1997 | Gianotti et al. | |
| 5,628,783 A | 5/1997 | Quiachon et al. | |
| 5,632,772 A | 5/1997 | Alcime et al. | |
| 5,636,641 A | 6/1997 | Fariabi | |
| 5,667,522 A | 9/1997 | Flomenblit et al. | |
| 5,674,276 A | 10/1997 | Andersen et al. | |
| 5,683,451 A | 11/1997 | Lenker et al. | |
| 5,690,120 A | 11/1997 | Jacobsen et al. | |
| 5,690,644 A | 11/1997 | Yurek et al. | |
| 5,695,499 A | 12/1997 | Helgerson et al. | |
| 5,700,269 A | 12/1997 | Pinchuk et al. | |
| 5,702,418 A | 12/1997 | Ravenscroft | |
| 5,709,702 A | 1/1998 | Cogita | |
| 5,709,703 A | 1/1998 | Lukic et al. | |
| 5,718,159 A * | 2/1998 | Thompson | 87/33 |
| 5,725,570 A | 3/1998 | Heath | |
| 5,733,327 A | 3/1998 | Igaki et al. | |
| 5,735,859 A | 4/1998 | Fischell et al. | |
| 5,741,325 A * | 4/1998 | Chaikof et al. | 623/1.35 |
| 5,749,883 A | 5/1998 | Halpern | |
| 5,749,920 A | 5/1998 | Quiachon et al. | |
| 5,769,884 A | 6/1998 | Solovay | |
| 5,769,885 A | 6/1998 | Quiachon et al. | |
| 5,776,099 A | 7/1998 | Tremulis | |
| 5,776,142 A | 7/1998 | Gunderson | |
| 5,782,909 A | 7/1998 | Quiachon et al. | |
| 5,797,952 A | 8/1998 | Klein | |
| 5,800,518 A | 9/1998 | Piplani et al. | |
| 5,810,837 A | 9/1998 | Hofmann et al. | |
| 5,817,102 A | 10/1998 | Johnson et al. | |
| 5,824,039 A | 10/1998 | Piplani et al. | |
| 5,824,041 A | 10/1998 | Lenker et al. | |
| 5,824,044 A | 10/1998 | Quiachon et al. | |
| 5,824,058 A | 10/1998 | Ravenscroft et al. | |
| 5,833,632 A | 11/1998 | Jacobsen et al. | |
| 5,836,868 A | 11/1998 | Ressemann et al. | |
| 5,868,754 A | 2/1999 | Levine et al. | |
| 5,888,201 A | 3/1999 | Stinson et al. | |
| 5,902,266 A | 5/1999 | Leone et al. | |
| 5,906,640 A | 5/1999 | Penn et al. | |
| 5,911,717 A | 6/1999 | Jacobsen et al. | |
| 5,916,194 A | 6/1999 | Jacobsen et al. | |
| 5,919,204 A | 7/1999 | Lukic et al. | |
| 5,928,260 A | 7/1999 | Chin et al. | |
| 5,951,599 A * | 9/1999 | McCrory | 606/108 |
| 5,957,973 A | 9/1999 | Quiachon et al. | |
| 5,957,974 A | 9/1999 | Thompson et al. | |
| 5,964,797 A | 10/1999 | Ho | |
| 5,980,530 A | 11/1999 | Willard et al. | |
| 5,980,533 A | 11/1999 | Holman | |
| 6,012,277 A * | 1/2000 | Prins et al. | 57/315 |
| 6,014,919 A | 1/2000 | Jacobsen et al. | |
| 6,015,432 A | 1/2000 | Rakos et al. | |
| 6,017,319 A | 1/2000 | Jacobsen et al. | |
| 6,019,778 A | 2/2000 | Wilson et al. | |
| 6,019,786 A | 2/2000 | Thompson | |
| 6,022,369 A | 2/2000 | Jacobsen et al. | |
| 6,024,754 A | 2/2000 | Engelson | |
| 6,024,763 A | 2/2000 | Lenker et al. | |
| 6,027,516 A | 2/2000 | Kolobow et al. | |
| 6,039,758 A | 3/2000 | Quiachon et al. | |
| 6,042,589 A | 3/2000 | Marianne | |
| 6,051,021 A | 4/2000 | Frid | |
| 6,056,993 A | 5/2000 | Leidner et al. | |
| 6,063,111 A | 5/2000 | Hieshima et al. | |
| 6,074,407 A | 6/2000 | Levine et al. | |
| 6,077,295 A | 6/2000 | Limon et al. | |
| 6,093,199 A | 7/2000 | Brown et al. | |
| 6,096,052 A | 8/2000 | Callister et al. | |
| 6,102,942 A | 8/2000 | Ahari | |
| 6,123,712 A | 9/2000 | Di Caprio et al. | |
| 6,126,685 A | 10/2000 | Lenker et al. | |
| 6,132,459 A | 10/2000 | Piplani et al. | |
| 6,139,543 A | 10/2000 | Esch et al. | |
| 6,146,415 A | 11/2000 | Fitz | |
| 6,149,680 A | 11/2000 | Shelso et al. | |
| 6,168,592 B1 | 1/2001 | Kupiecki et al. | |
| 6,183,410 B1 | 2/2001 | Jacobsen et al. | |
| 6,183,508 B1 | 2/2001 | Stinson et al. | |
| 6,197,046 B1 | 3/2001 | Piplani et al. | |
| 6,206,868 B1 | 3/2001 | Parodi | |
| 6,210,400 B1 | 4/2001 | Hebert et al. | |
| 6,210,434 B1 | 4/2001 | Quiachon et al. | |
| 6,210,435 B1 | 4/2001 | Piplani et al. | |
| 6,214,038 B1 | 4/2001 | Piplani et al. | |
| 6,214,042 B1 | 4/2001 | Jacobsen et al. | |
| 6,221,102 B1 | 4/2001 | Baker et al. | |
| 6,224,609 B1 | 5/2001 | Ressemann et al. | |
| 6,224,829 B1 | 5/2001 | Piplani et al. | |
| 6,231,598 B1 | 5/2001 | Berry et al. | |
| 6,235,050 B1 | 5/2001 | Quiachon et al. | |
| 6,241,759 B1 | 6/2001 | Piplani et al. | |
| 6,245,103 B1 | 6/2001 | Stinson | |
| 6,251,132 B1 | 6/2001 | Ravenscroft et al. | |
| 6,260,458 B1 | 7/2001 | Jacobsen et al. | |
| 6,261,305 B1 | 7/2001 | Marotta et al. | |
| 6,270,523 B1 | 8/2001 | Herweck et al. | |
| 6,280,465 B1 | 8/2001 | Cryer | |
| 6,287,331 B1 | 9/2001 | Heath | |
| 6,290,721 B1 | 9/2001 | Heath | |
| 6,302,810 B2 | 10/2001 | Yokota | |
| 6,302,893 B1 | 10/2001 | Limon et al. | |
| 6,322,576 B1 | 11/2001 | Wallace et al. | |
| 6,322,586 B1 | 11/2001 | Monroe et al. | |
| 6,322,587 B1 | 11/2001 | Quiachon et al. | |
| 6,344,041 B1 | 2/2002 | Kupiecki et al. | |
| 6,348,063 B1 | 2/2002 | Yassour et al. | |
| 6,350,199 B1 | 2/2002 | Williams et al. | |
| 6,350,278 B1 | 2/2002 | Lenker et al. | |
| 6,355,061 B1 | 3/2002 | Quiachon et al. | |
| 6,368,344 B1 | 4/2002 | Fitz | |
| 6,368,557 B1 | 4/2002 | Piplani et al. | |
| 6,375,670 B1 | 4/2002 | Greenhalgh | |
| 6,375,676 B1 | 4/2002 | Cox | |
| 6,379,618 B1 | 4/2002 | Piplani et al. | |
| 6,380,457 B1 | 4/2002 | Yurek et al. | |
| 6,389,946 B1 * | 5/2002 | Frid | 87/11 |
| 6,395,017 B1 | 5/2002 | Dwyer et al. | |
| 6,395,022 B1 | 5/2002 | Piplani et al. | |
| 6,398,802 B1 | 6/2002 | Yee | |
| 6,409,683 B1 | 6/2002 | Fonseca et al. | |
| 6,413,235 B1 | 7/2002 | Parodi | |
| 6,416,536 B1 | 7/2002 | Yee | |
| 6,428,489 B1 | 8/2002 | Jacobsen et al. | |
| 6,440,088 B1 | 8/2002 | Jacobsen et al. | |
| 6,443,971 B1 | 9/2002 | Boylan et al. | |
| 6,443,979 B1 | 9/2002 | Stalker et al. | |

| Patent No. | Date | Inventor |
|---|---|---|
| 6,454,999 B1 | 9/2002 | Farhangnia et al. |
| 6,478,778 B1 | 11/2002 | Jacobsen et al. |
| 6,482,221 B1 | 11/2002 | Hebert et al. |
| 6,491,648 B1 | 12/2002 | Cornish et al. |
| 6,497,711 B1 | 12/2002 | Plaia et al. |
| 6,503,450 B1 | 1/2003 | Afzal et al. |
| 6,514,261 B1 | 2/2003 | Randall et al. |
| 6,524,299 B1 | 2/2003 | Tran et al. |
| 6,527,763 B2 | 3/2003 | Esch et al. |
| 6,533,811 B1 | 3/2003 | Ryan |
| 6,540,778 B1 | 4/2003 | Quiachon et al. |
| 6,547,779 B2 | 4/2003 | Levine et al. |
| 6,551,352 B2 * | 4/2003 | Clerc et al. ............ 623/1.2 |
| 6,572,646 B1 | 6/2003 | Boylan et al. |
| 6,576,006 B2 | 6/2003 | Limon et al. |
| 6,582,460 B1 | 6/2003 | Cryer |
| 6,589,273 B1 | 7/2003 | McDermott |
| 6,592,616 B1 | 7/2003 | Stack et al. |
| 6,602,271 B2 | 8/2003 | Adams et al. |
| 6,602,280 B2 | 8/2003 | Chobotov |
| 6,605,110 B2 | 8/2003 | Harrison |
| 6,613,075 B1 | 9/2003 | Healy et al. |
| 6,622,604 B1 | 9/2003 | Chouinard et al. |
| 6,623,518 B2 | 9/2003 | Thompson et al. |
| 6,635,068 B1 | 10/2003 | Dubrul et al. |
| 6,638,243 B2 | 10/2003 | Kupiecki |
| 6,645,240 B2 | 11/2003 | Yee |
| 6,646,218 B1 | 11/2003 | Campbell et al. |
| 6,652,508 B2 | 11/2003 | Griffin et al. |
| 6,656,212 B2 | 12/2003 | Ravenscroft et al. |
| 6,656,218 B1 | 12/2003 | Denardo et al. |
| 6,660,024 B1 | 12/2003 | Flaherty |
| 6,663,666 B1 | 12/2003 | Quiachon et al. |
| 6,669,719 B2 | 12/2003 | Wallace et al. |
| 6,673,089 B1 | 1/2004 | Yassour et al. |
| 6,673,100 B2 | 1/2004 | Diaz et al. |
| 6,679,893 B1 | 1/2004 | Tran |
| 6,682,557 B1 | 1/2004 | Quiachon et al. |
| 6,685,735 B1 | 2/2004 | Ahari |
| 6,689,120 B1 * | 2/2004 | Gerdts ............ 604/526 |
| 6,689,162 B1 | 2/2004 | Thompson |
| 6,709,454 B1 | 3/2004 | Cox et al. |
| 6,712,834 B2 | 3/2004 | Yassour et al. |
| 6,726,700 B1 | 4/2004 | Levine |
| 6,733,519 B2 | 5/2004 | Lashinski et al. |
| 6,740,105 B2 | 5/2004 | Yodfat et al. |
| 6,740,112 B2 | 5/2004 | Yodfat et al. |
| 6,743,219 B1 | 6/2004 | Dwyer et al. |
| 6,755,855 B2 | 6/2004 | Yurek et al. |
| 6,758,885 B2 | 7/2004 | Leffel et al. |
| 6,767,361 B2 | 7/2004 | Quiachon et al. |
| 6,773,446 B1 | 8/2004 | Dwyer et al. |
| 6,793,667 B2 | 9/2004 | Hebert et al. |
| 6,814,748 B1 | 11/2004 | Baker et al. |
| 6,818,006 B2 | 11/2004 | Douk et al. |
| 6,833,003 B2 | 12/2004 | Jones et al. |
| 6,849,084 B2 | 2/2005 | Rabkin et al. |
| 6,858,034 B1 | 2/2005 | Hijlkema et al. |
| 6,860,893 B2 | 3/2005 | Wallace et al. |
| 6,860,898 B2 | 3/2005 | Stack et al. |
| 6,860,901 B1 | 3/2005 | Baker et al. |
| 6,866,677 B2 | 3/2005 | Douk et al. |
| 6,866,680 B2 | 3/2005 | Yassour et al. |
| 6,887,267 B2 | 5/2005 | Dworschak et al. |
| 6,890,337 B2 | 5/2005 | Feeser et al. |
| 6,955,685 B2 | 10/2005 | Escamilla et al. |
| 6,960,227 B2 | 11/2005 | Jones et al. |
| 6,964,670 B1 | 11/2005 | Shah et al. |
| 6,976,991 B2 | 12/2005 | Hebert et al. |
| 6,989,024 B2 | 1/2006 | Hebert et al. |
| 6,994,721 B2 | 2/2006 | Israel |
| 7,001,422 B2 | 2/2006 | Escamilla et al. |
| 7,004,964 B2 | 2/2006 | Thompson et al. |
| 7,011,675 B2 | 3/2006 | Hemerick et al. |
| 7,037,330 B1 | 5/2006 | Rivelli, Jr. et al. |
| 7,066,951 B2 | 6/2006 | Chobotov |
| 7,069,835 B2 | 7/2006 | Nishri et al. |
| 7,074,236 B2 | 7/2006 | Rabkin et al. |
| 7,093,527 B2 | 8/2006 | Rapaport et al. |
| 7,101,392 B2 | 9/2006 | Heath |
| 7,107,105 B2 | 9/2006 | Bjorklund et al. |
| 7,118,539 B2 | 10/2006 | Vrba et al. |
| 7,118,594 B2 | 10/2006 | Quiachon et al. |
| 7,122,050 B2 | 10/2006 | Randall et al. |
| 7,137,990 B2 | 11/2006 | Hebert et al. |
| 7,166,125 B1 | 1/2007 | Baker et al. |
| 7,169,170 B2 | 1/2007 | Widenhouse |
| 7,169,172 B2 | 1/2007 | Levine et al. |
| 7,172,617 B2 | 2/2007 | Colgan et al. |
| 7,195,639 B2 | 3/2007 | Quiachon et al. |
| 7,195,648 B2 | 3/2007 | Jones et al. |
| 7,201,768 B2 | 4/2007 | Diaz et al. |
| 7,201,769 B2 | 4/2007 | Jones et al. |
| 7,211,109 B2 | 5/2007 | Thompson |
| 7,213,495 B2 | 5/2007 | McCullagh et al. |
| 7,220,271 B2 | 5/2007 | Clubb et al. |
| 7,235,096 B1 | 6/2007 | Van Tassel et al. |
| 7,264,632 B2 | 9/2007 | Wright et al. |
| 7,275,471 B2 | 10/2007 | Nishri et al. |
| 7,279,005 B2 | 10/2007 | Stinson |
| 7,279,208 B1 | 10/2007 | Goffena et al. |
| 7,294,137 B2 | 11/2007 | Rivelli, Jr. et al. |
| 7,294,146 B2 | 11/2007 | Chew et al. |
| 7,300,456 B2 | 11/2007 | Andreas et al. |
| 7,300,460 B2 | 11/2007 | Levine et al. |
| 7,306,624 B2 | 12/2007 | Yodfat et al. |
| 7,309,351 B2 | 12/2007 | Escamilla et al. |
| 7,311,031 B2 | 12/2007 | McCullagh et al. |
| 7,320,702 B2 | 1/2008 | Hammersmark et al. |
| 7,323,001 B2 | 1/2008 | Clubb et al. |
| 7,331,973 B2 | 2/2008 | Gesswein et al. |
| 7,331,976 B2 | 2/2008 | McGuckin, Jr. et al. |
| 7,331,985 B2 | 2/2008 | Thompson et al. |
| 7,338,518 B2 | 3/2008 | Chobotov |
| 7,468,070 B2 | 12/2008 | Henry et al. |
| 7,470,282 B2 | 12/2008 | Shelso |
| 7,473,271 B2 | 1/2009 | Gunderson |
| 7,491,224 B2 | 2/2009 | Cox et al. |
| 2001/0044651 A1 | 11/2001 | Steinke et al. |
| 2001/0049547 A1 | 12/2001 | Moore |
| 2002/0062091 A1 | 5/2002 | Jacobsen et al. |
| 2002/0078808 A1 | 6/2002 | Jacobsen et al. |
| 2002/0087119 A1 | 7/2002 | Parodi |
| 2002/0120323 A1 | 8/2002 | Thompson et al. |
| 2003/0069522 A1 | 4/2003 | Jacobsen et al. |
| 2003/0100945 A1 | 5/2003 | Yodfat et al. |
| 2003/0135258 A1 | 7/2003 | Andreas et al. |
| 2003/0163155 A1 | 8/2003 | Haverkost et al. |
| 2003/0163156 A1 | 8/2003 | Hebert et al. |
| 2004/0024416 A1 | 2/2004 | Yodfat et al. |
| 2004/0044395 A1 | 3/2004 | Nelson |
| 2004/0073300 A1 | 4/2004 | Chouinard et al. |
| 2004/0088037 A1 | 5/2004 | Nachreiner et al. |
| 2004/0093010 A1 | 5/2004 | Gesswein et al. |
| 2004/0098099 A1 | 5/2004 | McCullagh et al. |
| 2004/0162606 A1 | 8/2004 | Thompson |
| 2004/0193178 A1 | 9/2004 | Nikolchev |
| 2004/0193179 A1 | 9/2004 | Nikolchev |
| 2004/0199243 A1 | 10/2004 | Yodfat |
| 2004/0215332 A1 | 10/2004 | Frid |
| 2004/0220585 A1 | 11/2004 | Nikolchev |
| 2004/0220663 A1 | 11/2004 | Rivelli |
| 2004/0254628 A1 * | 12/2004 | Nazzaro et al. ............ 623/1.13 |
| 2005/0090888 A1 | 4/2005 | Hines et al. |
| 2005/0137680 A1 * | 6/2005 | Ortiz et al. ............ 623/1.16 |
| 2005/0209672 A1 | 9/2005 | George et al. |
| 2005/0246010 A1 | 11/2005 | Alexander et al. |
| 2005/0267568 A1 | 12/2005 | Berez |
| 2005/0283220 A1 | 12/2005 | Gobran et al. |
| 2005/0288764 A1 | 12/2005 | Snow et al. |
| 2005/0288766 A1 | 12/2005 | Plain et al. |
| 2006/0036309 A1 | 2/2006 | Hebert et al. |
| 2006/0089703 A1 | 4/2006 | Escamilla et al. |
| 2006/0095213 A1 | 5/2006 | Escamilla et al. |
| 2006/0111771 A1 | 5/2006 | Ton et al. |
| 2006/0116750 A1 | 6/2006 | Hebert et al. |
| 2006/0184238 A1 * | 8/2006 | Kaufmann et al. ............ 623/1.53 |
| 2006/0206200 A1 | 9/2006 | Garcia et al. |

| | | | |
|---|---|---|---|
| 2006/0206201 A1 | 9/2006 | Garcia et al. | |
| 2006/0212127 A1 | 9/2006 | Karabey et al. | |
| 2006/0271149 A1 | 11/2006 | Berez et al. | |
| 2006/0271153 A1 | 11/2006 | Garcia et al. | |
| 2007/0021816 A1 | 1/2007 | Rudin | |
| 2007/0043419 A1 | 2/2007 | Nikolchev et al. | |
| 2007/0060994 A1* | 3/2007 | Gobran et al. | 623/1.4 |
| 2007/0073379 A1 | 3/2007 | Chang | |
| 2007/0100414 A1 | 5/2007 | Licata et al. | |
| 2007/0112415 A1 | 5/2007 | Bartlett | |
| 2007/0119295 A1 | 5/2007 | McCullagh et al. | |
| 2007/0123969 A1 | 5/2007 | Gianotti | |
| 2007/0162104 A1 | 7/2007 | Frid | |
| 2007/0167980 A1 | 7/2007 | Figulla et al. | |
| 2007/0198076 A1 | 8/2007 | Hebert et al. | |
| 2007/0203559 A1 | 8/2007 | Freudenthal et al. | |
| 2007/0203563 A1 | 8/2007 | Hebert et al. | |
| 2007/0208376 A1 | 9/2007 | Meng | |
| 2007/0225760 A1 | 9/2007 | Moszner et al. | |
| 2007/0299500 A1 | 12/2007 | Hebert et al. | |
| 2007/0299501 A1 | 12/2007 | Hebert et al. | |
| 2007/0299502 A1 | 12/2007 | Hebert et al. | |
| 2008/0039930 A1* | 2/2008 | Jones et al. | 623/1.15 |
| 2008/0039933 A1 | 2/2008 | Yodfat et al. | |
| 2008/0082154 A1 | 4/2008 | Tseng et al. | |
| 2008/0114391 A1* | 5/2008 | Dieck et al. | 606/200 |
| 2008/0208320 A1 | 8/2008 | Tan-Malecki et al. | |
| 2008/0221666 A1 | 9/2008 | Licata et al. | |
| 2008/0221671 A1* | 9/2008 | Chouinard et al. | 623/1.53 |
| 2008/0255654 A1 | 10/2008 | Hebert et al. | |
| 2008/0255655 A1 | 10/2008 | Kusleika et al. | |
| 2008/0262590 A1 | 10/2008 | Murray | |
| 2008/0269774 A1 | 10/2008 | Garcia et al. | |
| 2008/0300667 A1 | 12/2008 | Hebert et al. | |
| 2009/0024202 A1 | 1/2009 | Dave et al. | |
| 2009/0024205 A1 | 1/2009 | Hebert et al. | |
| 2009/0030496 A1 | 1/2009 | Kaufmann et al. | |
| 2009/0030497 A1 | 1/2009 | Metcalf et al. | |
| 2009/0105802 A1 | 4/2009 | Henry et al. | |
| 2009/0105803 A1 | 4/2009 | Shelso | |
| 2009/0125093 A1 | 5/2009 | Hansen | |
| 2009/0192536 A1 | 7/2009 | Berez et al. | |
| 2009/0198318 A1 | 8/2009 | Berez et al. | |
| 2009/0270974 A1 | 10/2009 | Berez et al. | |
| 2009/0287241 A1 | 11/2009 | Berez et al. | |
| 2009/0287288 A1 | 11/2009 | Berez et al. | |
| 2009/0292348 A1 | 11/2009 | Berez et al. | |
| 2009/0318947 A1 | 12/2009 | Garcia et al. | |
| 2009/0319017 A1 | 12/2009 | Berez et al. | |
| 2010/0010624 A1 | 1/2010 | Berez et al. | |
| 2010/0179583 A1 | 7/2010 | Carpenter et al. | |
| 2010/0179647 A1 | 7/2010 | Carpenter et al. | |

FOREIGN PATENT DOCUMENTS

| | | |
|---|---|---|
| JP | 10-328216 | 12/1998 |
| JP | 11-299901 A | 2/1999 |
| JP | 11-506686 | 6/1999 |
| JP | 2001-509412 | 7/2001 |
| JP | 2003520103 A | 7/2003 |
| JP | 2006-506201 | 2/2006 |
| WO | WO-88/00813 A1 | 2/1988 |
| WO | WO-95/09586 A1 | 4/1995 |
| WO | WO-99/02092 A1 | 1/1999 |
| WO | WO 99/49812 | 10/1999 |
| WO | WO 01/05331 | 1/2001 |
| WO | WO-0152771 A1 | 7/2001 |
| WO | WO-0205729 A2 | 1/2002 |
| WO | WO-02/47579 A1 | 6/2002 |
| WO | WO-03/007840 A2 | 1/2003 |
| WO | WO 03/049600 | 6/2003 |
| WO | WO 2005/023149 | 3/2005 |
| WO | WO 2005/115118 | 12/2005 |
| WO | WO-2007139689 A2 | 12/2007 |
| WO | WO-2007139699 A2 | 12/2007 |

OTHER PUBLICATIONS

Brilstra, et al., Treatment of Intracranial Aneurysms by Embolization with Coils: A Systematic Review, Stroke, Journal of the American Heart Association, 1999, vol. 30, pp. 470-476.

Ferguson, Gary, Physical Factors in the Initiation, Growth and Rupture of Human Intracranial Saccular Aneurysms, J. Neurosurg, Dec. 1972, vol. 37, pp. 666-667.

Geremia, et al., Embolization of Experimentally Created Aneurysms with Intravascular Stent Devices, ANJR American Journal of Neuroradiology, Aug. 1994, vol. 15, pp. 1223-1231.

Geremia, et al., Occlusion of Experimentally Created Fusiform Aneurysms with Porous Metallic Stents, ANJR Am J Neuroradiol, Apr. 2000, Issue 21, pp. 739-745.

Lanzino, et al., Efficacy and Current Limitations of Intravascular Stents for Intracranial Internal Carotid, Vertebral, and Basilar Artery Aneurysms, Journal of Neurosurgery, Oct. 1999, vol. 91, Issue 4, pp. 538-546.

Lieber, et al., Alteration of Hemodynamics in Aneurysm Models by Stenting: Influence of Stent Porosity, Ann of Biomedical Eng., 1997, vol. 25, pp. 460-469, Buffalo, NY.

Lieber, et al., The Physics of Endoluminal Stenting in the Treatment of Cerebrovascular Aneurysms, Neurological Research, 2002, Vcol 24, Issue Supplement 1, pp. S32-S42.

Moss, et al., Vascular Occlusion with a Balloon-Expadable Stent Occluder, Radiology, May 1994, vol. 191, Issue 2, pp. 483-486.

Pereira, Edgard, History of Endovascular Aneurysm Occlusion, Management of Cerebral Aneurysms, 2004, pp. 11-26.

Steiger, Pathophysiology of Development and Rupture of Cerebral Aneurysms, Acta Nurochirurgica, Mar. 1990, vol. Supplementum 48, Pages in 62 pages.

Qureshi, Adnan, Endovascular Treatment of Cerebrovascular Diseases and Intracranial Neoplasms, The Lancelet, Mar. 2004, vol. 363, pp. 804-813.

Tenaglia, et al., Ultrasound Guide Wire-Directed Stent Deployment, Duke University Medical Center, Department of Medicine, 1993 USA.

Yu, et al., A Steady Flow Analysis on the Stented and Non-Stented Sidewall Aneurysm Models, Medical Engineering and Physics, Apr. 1999, Issue 21, pp. 133-141.

* cited by examiner

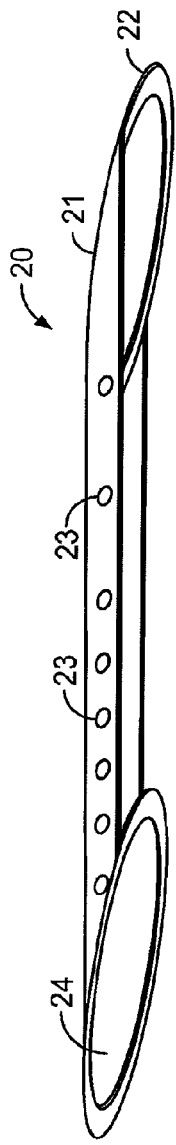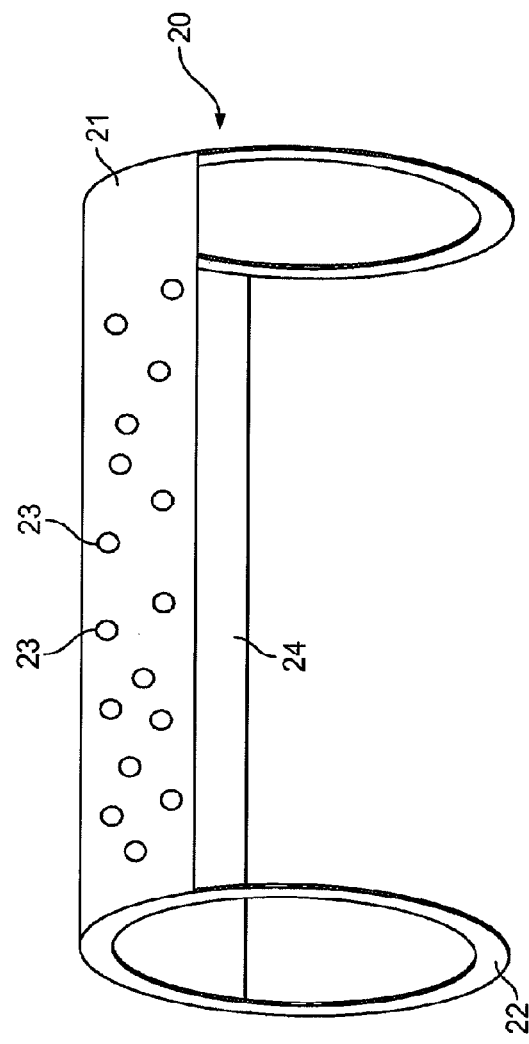
FIG. 2A
FIG. 2B

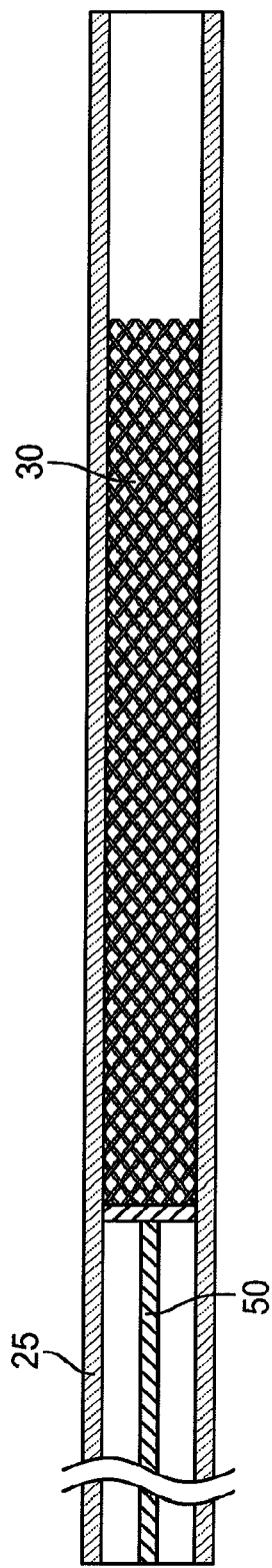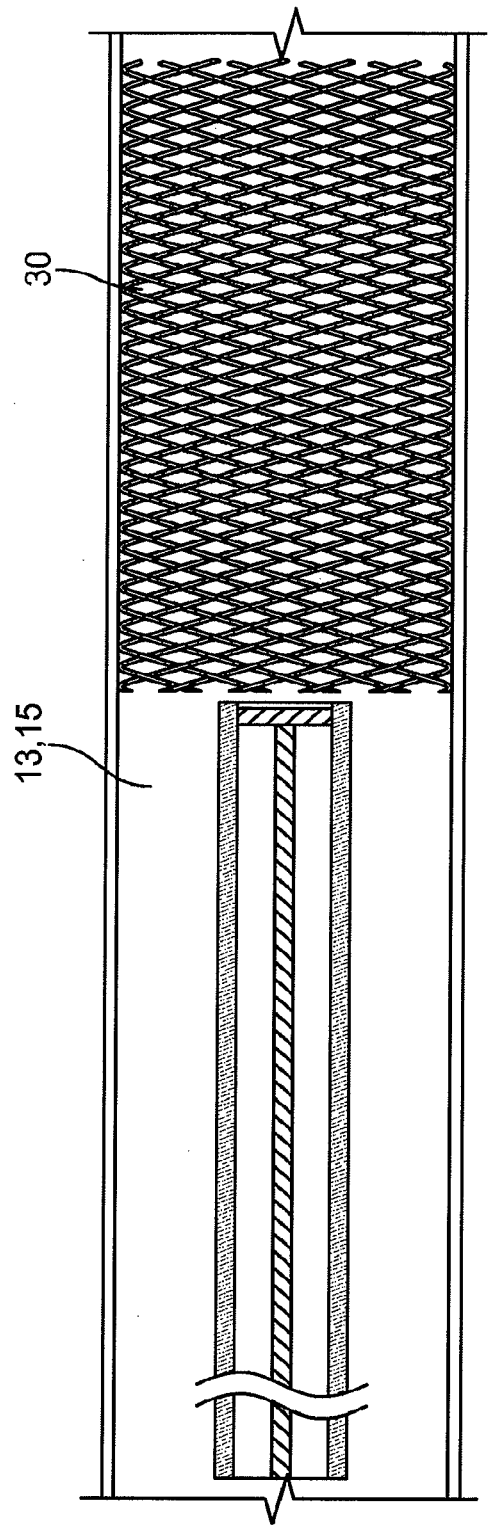

FLEXIBLE VASCULAR OCCLUDING DEVICE

RELATED APPLICATION

This application is a divisional of U.S. application Ser. No. 11/420,025, which is a continuation-in-part of and claims priority to U.S. application Ser. No. 11/136,395, filed May 25, 2005, which claims the benefit of U.S. Provisional Application Ser. No. 60/574,429, entitled "Flexible Vascular Prosthesis," filed May 25, 2004. Each of these applications is expressly incorporated herein by reference in their entireties.

FIELD OF THE INVENTION

The invention relates generally to an implantable device that could be used in the vasculature to treat common vascular malformations. More particularly, it relates to a flexible, biocompatible device that can be introduced into the vasculature of a patient to embolize and occlude aneurysms, particularly cerebral aneurysms.

BACKGROUND OF THE INVENTION

Walls of the vasculature, particularly arterial walls, may develop pathological dilatation called an aneurysm. Aneurysms are commonly observed as a ballooning-out of the wall of an artery. This is a result of the vessel wall being weakened by disease, injury or a congenital abnormality. Aneurysms have thin, weak walls and have a tendency to rupture and are often caused or made worse by high blood pressure. Aneurysms could be found in different parts of the body; the most common being abdominal aortic aneurysms (AAA) and the brain or cerebral aneurysms. The mere presence of an aneurysm is not always life-threatening, but they can have serious heath consequences such as a stroke if one should rupture in the brain. Additionally, as is known, a ruptured aneurysm can also result in death.

The most common type of cerebral aneurysm is called a saccular aneurysm, which is commonly found at the bifurcation of a vessel. The locus of bifurcation, the bottom of the V in the Y, could be weakened by hemodynamic forces of the blood flow. On a histological level, aneurysms are caused by damage to cells in the arterial wall. Damage is believed to be caused by shear stresses due to blood flow. Shear stress generates heat that breaks down the cells. Such hemodynamic stresses at the vessel wall, possibly in conjunction with intrinsic abnormalities of the vessel wall, have been considered to be the underlying cause for the origin, growth and rupture of these saccular aneurysms of the cerebral arteries (Lieber and Gounis, The Physics of Endoluminal stenting in the Treatment of Cerebrovascular Aneurysms, Neurol Res 2002: 24: S32-S42). In histological studies, damaged intimal cells are elongated compared to round healthy cells. Shear stress can vary greatly at different phases of the cardiac cycle, locations in the arterial wall and among different individuals as a function of geometry of the artery and the viscosity, density and velocity of the blood. Once an aneurysm is formed, fluctuations in blood flow within the aneurysm are of critical importance because they can induce vibrations of the aneurysm wall that contribute to progression and eventual rupture. For a more detailed description of the above concepts see, for example, Steiger, Pathophysiology of Development and Rupture of Cerebral Aneurysms, Acta Neurochir Suppl 1990: 48: 1-57; Fergueson, Physical Factors in the Initiation, Growth and Rupture of Human Intracranial Saccular Aneurysms, J Neurosurg 1972: 37: 666-677.

Aneurysms are generally treated by excluding the weakened part of the vessel from the arterial circulation. For treating a cerebral aneurysm, such reinforcement is done in many ways: (i) surgical clipping, where a metal clip is secured around the base of the aneurysm; (ii) packing the aneurysm with microcoils, which are small, flexible wire coils; (iii) using embolic materials to "fill" an aneurysm; (iv) using detachable balloons or coils to occlude the parent vessel that supplies the aneurysm; and (v) endovascular stenting. For a general discussion and review of these different methods see Qureshi, Endovascular Treatment of Cerebrovascular Diseases and Intracranial Neoplasms, Lancet. 2004 Mar. 6; 363 (9411):804-13; Brilstra et al. Treatment of Intracranial Aneurysms by Embolization with Coils: A Systematic Review, Stroke 1999; 30: 470-476.

As minimally invasive interventional techniques gain more prominence, micro-catheter based approaches for treating neurovascular aneurysms are becoming more prevalent. Micro-catheters, whether flow-directed or wire-directed, are used for dispensing embolic materials, microcoils or other structures (e.g., stents) for embolization of the aneurysm. A microcoil can be passed through a micro-catheter and deployed in an aneurysm using mechanical or chemical detachment mechanisms, or be deployed into the parent vessel to permanently occlude it and thus block flow into the aneurysm. Alternatively, a stent could be tracked through the neurovasculature to the desired location. Article by Pereira, History of Endovascular Aneurysms Occlusion in Management of Cerebral Aneurysms; Eds: Le Roux et al., 2004, pp: 11-26 provides an excellent background on the history of aneurysm detection and treatment alternatives.

As noted in many of the articles mentioned above, and based on the origin, formation and rupture of the cerebral aneurysm, it is obvious that the goal of aneurysmal therapy is to reduce the risk of rupture of the aneurysm and thus the consequences of sub-arachnoid hemorrhage. It should also be noted that while preventing blood from flowing into the aneurysm is highly desirable, so that the weakened wall of the aneurysm doesn't rupture, it may also be vital that blood flow to the surrounding structures is not limited by the method used to obstruct blood flow to the aneurysm. Conventional stents developed for treating other vascular abnormalities in the body are ill suited for embolizing cerebral aneurysms. This could lead to all the usual complications when high oxygen consumers, such as brain tissue, are deprived of the needed blood flow.

There are many shortcomings with the existing approaches for treating neurovascular aneurysms. The vessels of the neurovasculature are the most tortuous in the body; certainly more tortuous than the vessels of the coronary circulation. Hence, it is a challenge for the surgeon to navigate the neurovasculature using stiff coronary stents that are sometimes used in the neurovasculature for treating aneurysms. The bending force of a prosthesis indicates the maneuverability of the prosthesis through the vasculature; a lower bending force would imply that the prosthesis is more easily navigated through the vasculature compared to one with a higher bending force. Bending force for a typical coronary stent is 0.05 lb-in (force to bend 0.5 inches cantilever to 90 degree). Hence, it will be useful to have neural prosthesis that is more flexible than existing stents.

Existing stent structures, whether used in coronary vessels or in the neurovasculature (microcoils) are usually straight, often laser cut from a straight tubing or braiding with stiff metallic materials. However, most of the blood vessels are curved. Hence, current stent structures and microcoils impart significant stress on the vessel walls as they try to straighten a curved vessel wall. For a weakened vessel wall, particularly where there is a propensity for an aneurysm formation, this could have disastrous consequences.

As noted earlier, the hemodynamic stress placed on the blood vessels, particularly at the point of bifurcation, leads to weakening of the vessel walls. The most significant source of such stress is the sudden change in direction of the blood flow. Hence, if one were to minimize the sudden change in direction of blood flow, particularly at the location of vessel weakness, it would be beneficial.

Existing approaches to occluding aneurysms could lead to another set of problems. Methods that merely occlude the aneurysm by packing or filling it with embolic material (coils or liquid polymers) do not address the fundamental flow abnormalities that contribute to the formation of aneurysm.

A stent structure could be expanded after being placed intraluminally on a balloon catheter. Alternatively, self-expanding stems could be inserted in a compressed state and expanded upon deployment. For balloon expandable stents, the stent is mounted on a balloon at the distal end of a catheter, the catheter is advanced to the desired location and the balloon is inflated to expand the stent into a permanent expanded condition. The balloon is then deflated and the catheter withdrawn leaving the expanded stent to maintain vessel patency. Because of the potentially lethal consequences of dissecting or rupturing an intracerebral vessel, the use of balloon expandable stents in the brain is fraught with problems. Proper deployment of a balloon expandable stent requires slight over expanding of the balloon mounted stent to embed the stent in the vessel wall and the margin of error is small. Balloon expandable stents are also poorly suited to adapt to the natural tapering of cerebral vessels which taper proximally to distally. If a stent is placed from a parent vessel into a smaller branch vessel the change in diameter between the vessels makes it difficult to safely deploy a balloon expandable stent. A self-expanding stent, where the compressed or collapsed stent is held by an outer restraining sheath over the compressed stent to maintain the compressed state until deployment. At the time of deployment, the restraining outer sheath is retracted to uncover the compressed stent, which then expands to keep the vessel open. Additionally, the catheters employed for delivering such prosthesis are micro-catheters with outer diameter of 0.65 mm to 1.3 mm compared to the larger catheters that are used for delivering the large coronary stents to the coronaries.

U.S. Pat. No. 6,669,719 (Wallace et al.) describes a stent and a stent catheter for intra-cranial use. A rolled sheet stent is releasably mounted on the distal tip of a catheter. Upon the rolled sheet being positioned at the aneurysm, the stent is released. This results in immediate and complete isolation of an aneurysm and surrounding side branches of the circulatory system and redirecting blood flow away from the aneurysm. A significant drawback of such a system is that the surrounding side branches, along with the target aneurysm, are deprived of the needed blood flow after the stent has been deployed.

U.S. Pat. No. 6,605,110 (Harrison) describes a self-expanding stent for delivery through a tortuous anatomy or for conforming the stent to a curved vessel. This patent describes a stent structure with radially expandable cylindrical elements arranged in parallel to each other and interspersed between these elements and connecting two adjacent cylindrical elements are struts that are bendable. While this structure could provide the necessary flexibility and bendability of the stent for certain applications, it is expensive and complex to manufacture.

U.S. Pat. No. 6,572,646 (Boylan) discloses a stent made up of a super-elastic alloy, such as Ni—Ti alloy (Nitinol), with a low temperature phase that induces a first shape to the stent and a high temperature phase that induces a second shape to the stent with a bend along the length. U.S. Pat. No. 6,689,162 (Thompson) discloses a braided prosthesis that uses strands of metal, for providing strength, and compliant textile strands. U.S. Pat. No. 6,656,218 (Denardo et al.) describes an intravascular flow modifier that allows microcoil introduction.

SUMMARY OF THE INVENTION

An aspect of the present invention provides a highly flexible implantable occluding device that can easily navigate the tortuous vessels of the neurovasculature. Additionally, occluding device can easily conform to the shape of the tortuous vessels of the vasculature. Furthermore, the occluding device can direct the blood flow within a vessel away from an aneurysm; additionally such an occluding device allows adequate blood flow to be provided to adjacent structures such that those structures, whether they are branch vessels or oxygen demanding tissues, are not deprived of the necessary blood flow.

The occluding device is also capable of altering blood flow to the aneurysm, yet maintaining the desired blood flow to the surrounding tissue and within the vessel. In this instance, some blood is still allowed to reach the aneurysm, but not enough to create a laminar flow within the aneurysm that would cause injury to its thinned walls. Instead, the flow would be intermittent, thereby providing sufficient time for blood clotting or filler material curing within the aneurysm.

The occluding device is flexible enough to closely approximate the native vasculature and conform to the natural tortuous path of the native blood vessels. One of the significant attributes of the occluding device according to the present invention is its ability to flex and bend, thereby assuming the shape of a vasculature within the brain. These characteristics are for a neurovascular occluding device than compared to a coronary stent, as the vasculature in the brain is smaller and more tortuous.

In general terms, aspects of the present invention relate to methods and devices for treating aneurysms. In particular, a method of treating an aneurysm with a neck comprises deploying a vascular occluding device in the lumen of a vessel at the location of the aneurysm, whereby the blood flow is redirected away from the neck of the aneurysm. The induced stagnation of the blood in the lumen of the aneurysm would create embolization in the aneurysm. The occluding device spans the width of the stem of the aneurysm such that it obstructs or minimizes the blood flow to the aneurysm. The occluding device is very flexible in both its material and its arrangement. As a result, the occluding device can be easily navigated through the tortuous blood vessels, particularly those in the brain. Because the occluding device is flexible, very little force is required to deflect the occluding device to navigate through the vessels of the neurovasculature, which is of significance to the operating surgeon.

A feature of the occluding device, apart from its flexibility, is that the occluding device may have an asymmetrical braid pattern with a higher concentration of braid strands or a different size of braid strands on the surface facing the neck of the aneurysm compared to the surface radially opposite to it. In one embodiment, the surface facing the aneurysm is almost impermeable and the diametrically opposed surface is highly permeable. Such a construction would direct blood flow away from the aneurysm, but maintain blood flow to the side branches of the main vessel in which the occluding device is deployed.

In another embodiment, the occluding device has an asymmetrical braid count along the longitudinal axis of the occluding device. This provides the occluding device with a natural tendency to curve, and hence conform to the curved blood vessel. This reduces the stress exerted by the occluding device on the vessel wall and thereby minimizing the chances of aneurysm rupture. Additionally, because the occluding device is naturally curved, this eliminates the need for the tip of the micro-catheter to be curved. Now, when the curved occluding device is loaded on to the tip of the micro-catheter, the tip takes the curved shape of the occluding device. The occluding device could be pre-mounted inside the micro-catheter and can be delivered using a plunger, which will push the occluding device out of the micro-catheter when desired. The occluding device could be placed inside the micro-catheter in a compressed state. Upon exiting the micro-catheter, it could expand to the size of the available lumen and maintain patency of the lumen and allow blood flow through the lumen. The occluding device could have a lattice structure and the size of the openings in the lattice could vary along the length of the occluding device. The size of the lattice openings can be controlled by the braid count used to construct the lattice.

According to one aspect of the invention, the occluding device can be used to remodel an aneurysm within the vessel by, for example, neck reconstruction or balloon remodeling. The occluding device can be used to form a barrier that retains occlusion material within the aneurysm so that introduced material will not escape from within the aneurysm due to the lattice density of the occluding device in the area of the aneurysm.

In another aspect of the invention, a device for occluding an aneurysm is disclosed. The device is a tubular with a plurality of perforations distributed on the wall of the member. The device is placed at the base of the aneurysm covering the neck of the aneurysm such that the normal flow to the body of the aneurysm is disrupted and thereby generating thrombus and ultimately occlusion of the aneurysm.

In yet another aspect of this invention, the device is a braided tubular member. The braided strands are ribbons with rectangular cross section, wires with a circular cross section or polymeric strands.

In another embodiment, a device with a braided structure is made in order to conform to a curved vessel in the body, where the density of the braid provides enough rigidity and radial strength. Additionally, the device can be compressed using a force less than 10 grams. This enables the device to be compliant with the artery as the arterial wall is pulsating. Also, the device is capable of bending upon applying a force of less than 5 gram/cm.

Other aspects of the invention include methods corresponding to the devices and systems described herein.

BRIEF DESCRIPTION OF THE DRAWINGS

The invention has other advantages and features which will be more readily apparent from the following detailed description of the invention and the appended claims, when taken in conjunction with the accompanying drawings, in which:

FIGS. 2A and 2B illustrate one embodiment of an occluding device to treat aneurysms.

FIG. 5 shows the occluding device in a compressed state inside a micro-catheter being advanced out of the micro-catheter using a plunger.

FIG. 6 shows the compressed occluding device shown in FIG. 5 deployed outside the micro-catheter and is in an expanded state.

DETAILED DESCRIPTION OF THE PREFERRED EMBODIMENTS

The devices shown in the accompanying drawings are intended for treating aneurysms. They are generally deployed, using micro-catheters, at the location of a cerebral aneurysm that is intended to be treated. One such system is disclosed in copending U.S. patent application titled "System and Method for Delivering and Deploying an Occluding Device Within a Vessel", U.S. Ser. No. 11/136,398 filed on May 25, 2005, which is incorporated herein by reference in its entirety. The embodiments of the endovascular occluding device according to aspects of the present invention is useful for treating cerebral aneurysms that are commonly treated using surgical clips, microcoils or other embolic devices.

Figure 1:
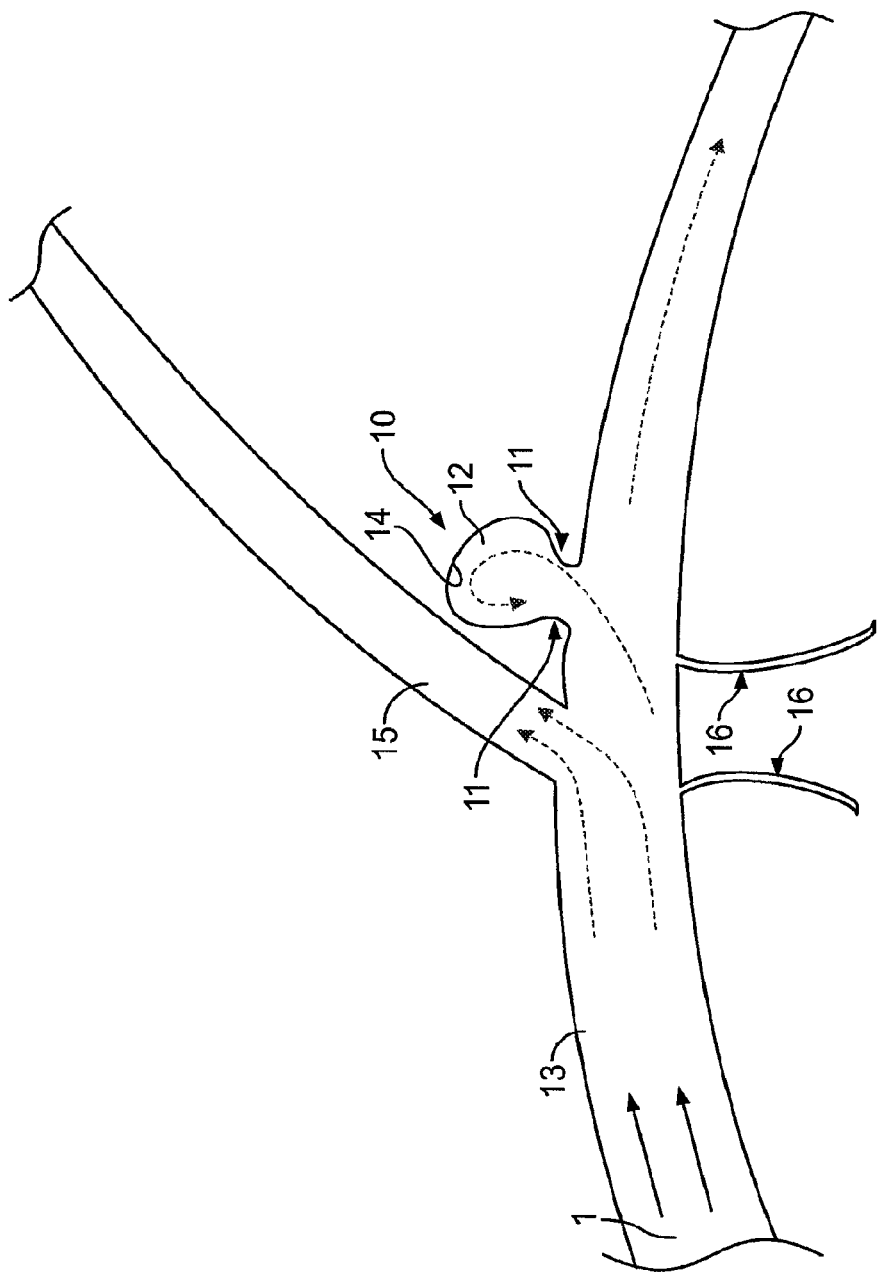
FIG. 1 is an illustration of an aneurysm, branch vessels and blood flow to the aneurysm.

FIG. 1 illustrates a typical cerebral aneurysm 10 in the brain. A neck 11 of the aneurysm 10 can typically define an opening of between about 2 to 25 mm. As is understood, the neck 11 connects the vessel 13 to the lumen 12 of the aneurysm 10. As can be seen in FIG. 1, the blood flow 1 within the vessel 13 is channeled through the lumen 12 and into the aneurysm. In response to the constant blood flow into the aneurysm, the wall 14 of lumen 12 continues to distend and presents a significant risk of rupturing. When the blood within the aneurysm 10 causes pressure against the wall 14 that exceeds the wall strength, the aneurysm ruptures. The present invention could prevent such ruptures. Also shown in FIG. 1 are the bifurcation 15 and the side branches 16.

FIG. 2 illustrates one embodiment of a vascular occluding device 20 in accordance with an aspect of the present invention. In the illustrated embodiment, the occluding device 20 has a substantially tubular structure 22 defined by an outer surface 21, an inner surface 24 and a thin wall that extends between the surfaces 21, 24. A plurality of openings 23 extend between the surfaces 21, 24 and allow for fluid flow from the interior of the occluding device 20 to the wall of the vessel. Occluding device 20 is radially compressible and longitudinally adjustable.

Figure 3:
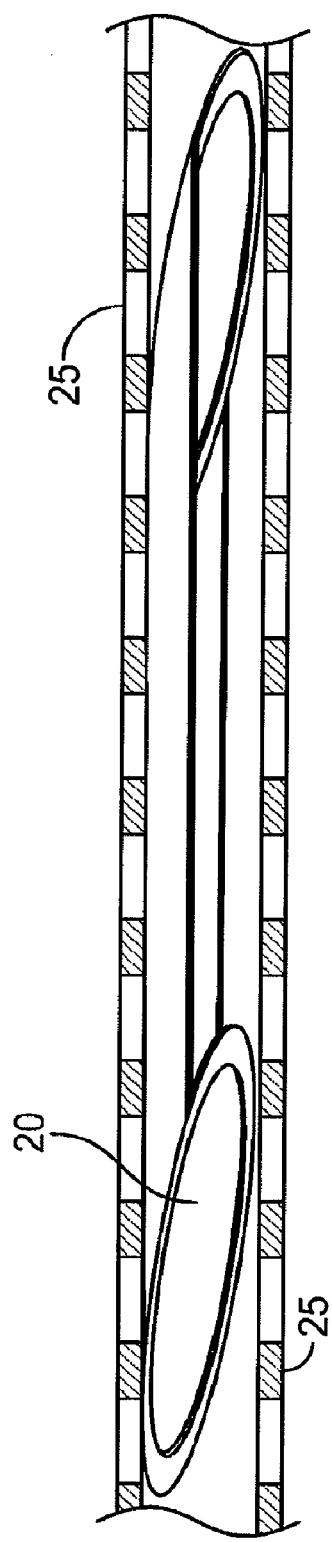
FIG. 3 is an illustration of the embodiment shown in FIG. 2 in a compressed state inside a micro-catheter.

FIG. 3 shows a micro-catheter 25 and the occluding device 20 inside the micro-catheter 25 in a compressed state prior to being released within the vasculature of the patient.

Figure 4A:
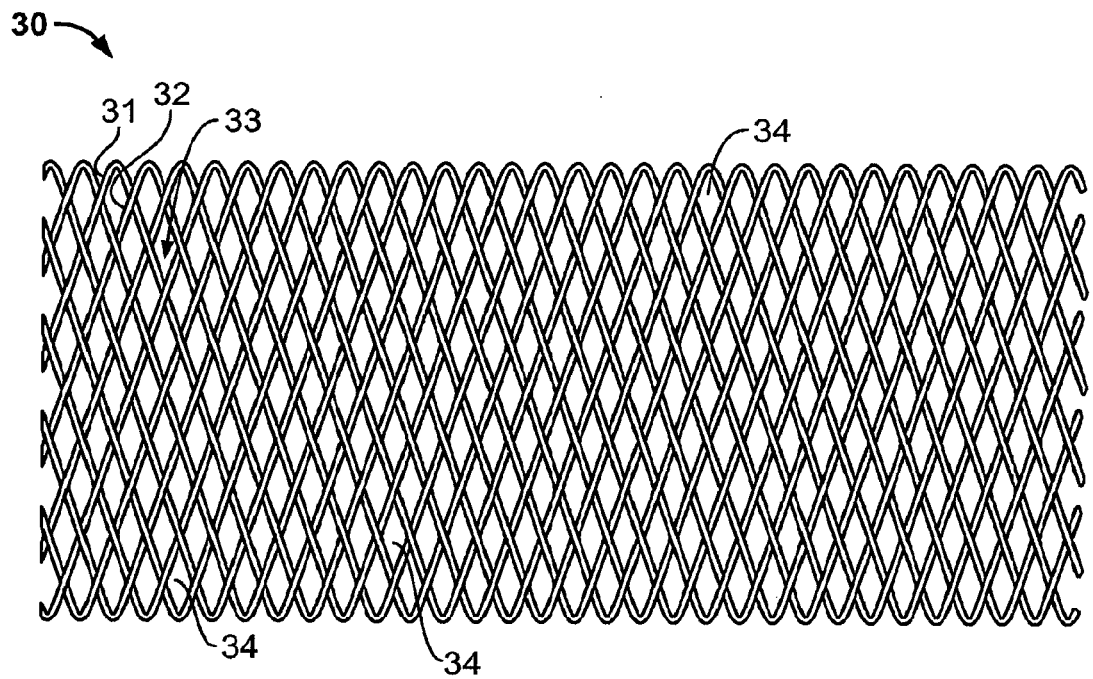
FIG. 4A is another embodiment of an occluding device for treating aneurysms.
Figure 4B:
FIGS. 4B and 4C illustrate cross sections of portions of ribbons that can be used to form the occluding device of FIG. 4A.

FIG. 4 illustrates another embodiment of the occluding device 30 having two or more strands of material(s) 31, 32 wound in a helical fashion. The braiding of such material in this fashion results in a lattice structure 33. As can be understood, the dimension of the lattice 33 and the formed interstices 34 is determined, at least in part, by the thickness of the strand materials, the number of strands and the number of helices per unit length of the occluding device 30. For example, the interstices 34 and/or the dimension of the lattice 33 may be determined by the number of strands of material(s) 31, 32 wound in helical fashion. In one example, any number of braiding ribbons up to 16 braiding ribbons may be used (e.g., 5, 8, 10, 13, 15 or 16 braiding ribbons). In another example, 16-32 braiding ribbons may be used (e.g., 20, 23, 25, 27, 30, or 32 braiding ribbons). In another example greater than 32 braiding ribbons may be used such as, for example, 35, 40, 48, 50, 55, 60, 80, 100, or greater braiding ribbons. Nevertheless, other values are possible.

Hence, strands of material, such as ribbons, may intersect to form a braid pattern. The intersection of the strand material may be formed in either a radial or axial direction on a surface of a forming device such as a braiding mandrel. When the intersection of the strand material is along an axial path, for example, the intersecting material may be at a fixed or variable frequency. As one example of strand material intersecting at a fixed frequency, the intersecting strand material may be along any 1.0 inch axial path on the surface of the forming device (e.g., a braiding mandrel) to indicate the pick count. When the intersection of the strand material is along a radial path or circumferential path, the spacing of the strand material may be uniformly or variably distributed. In one example of the strand material along a radial or circumferential path in which the spacing is uniformly distributed, the spacing along the radial direction may be determined based on the following formula:

$$(\pi)^*(\text{forming device diameter})/(\text{\#ribbons}/2) \quad \text{Eq. (1):}$$

Figure 17:
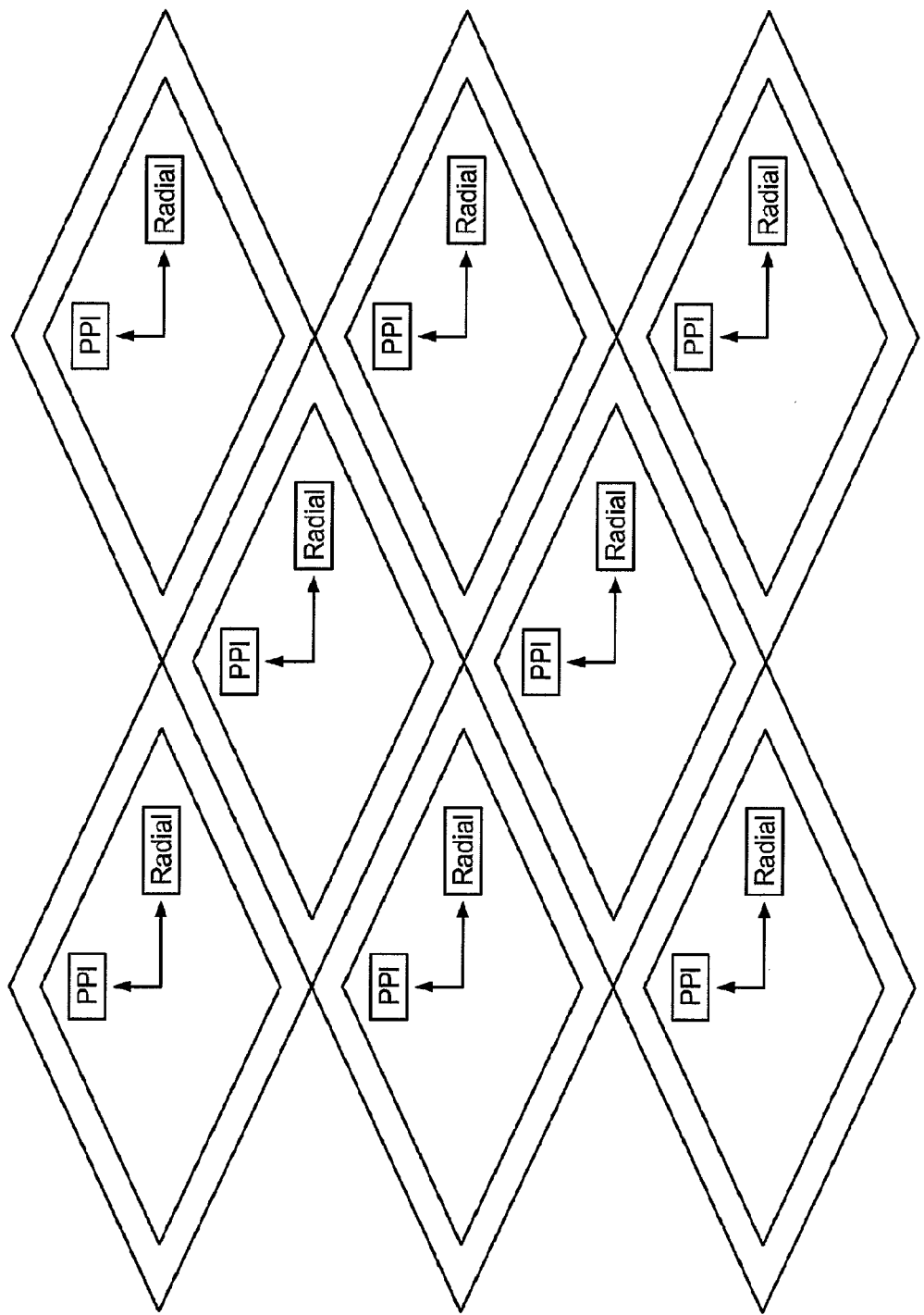
FIG. 17 illustrates an example of a mesh pattern of a lattice in an occluding device.
Figure 18:
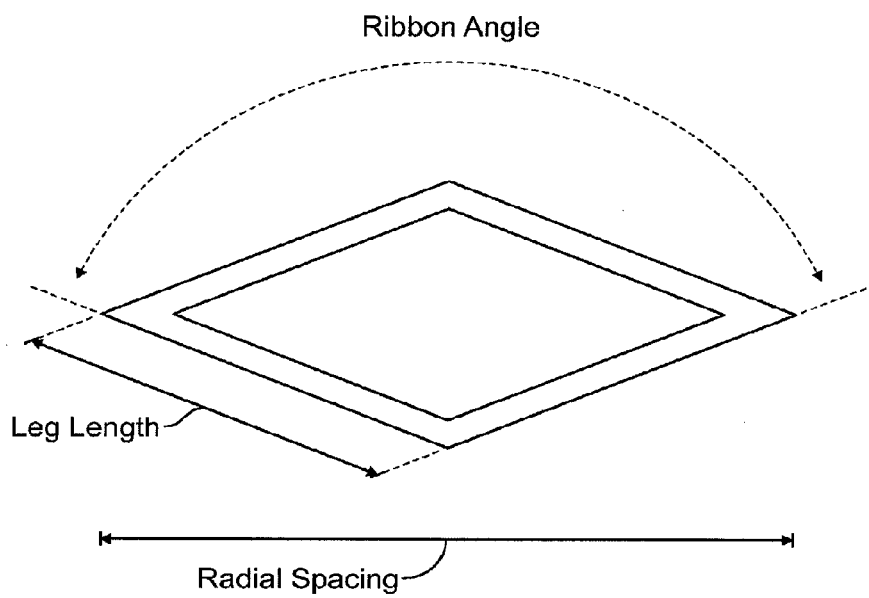
FIG. 18 illustrates an example of a braiding element of a lattice in an occluding device.

FIG. 18 illustrates an example of braiding elements or cells in the radial and PPI (picks per inch) directions. Any single element of the braid (i.e., braid element) may be combined to form a mesh pattern as illustrated in FIG. 17 on a surface of a forming device (e.g., braiding mandrel). The braid is capable of impeding or disrupting the flow of fluid (e.g., blood) in a vessel (e.g., blood vessel). The braid or lattice pattern, density, shape, etc. when the occluding device is deployed in the vessel, may at least partially determine the flow within the vessel. Each of the parameters of the braid or lattice may also be controlled by a user to control flow.

Parameters for determining the flow through an occluding device containing a lattice pattern, density, shape, etc. include surface coverage of the occluding device and cell size of the braid or lattice pattern. Each of these parameters may further characterize the geometry of the braid or lattice. Surface coverage may be determined as (surface area)/(total surface area), where the surface area is the surface area of the frame or solid element and the total surface area is of the entire element (i.e., frame and opening).

Cell size may be determined as the maximum length defining a cell opening. Braiding patterns that increase surface coverage while decreasing cell size may have an increased effect on disrupting or impeding the flow through the braid or lattice. Each of the parameters of surface coverage and cell size may further be enhanced by varying the width of the strand material (e.g., the ribbons), increasing the number of strands of strand material defining the braid, and/or increasing the PPI (i.e., Picks Per Inch).

The braiding or lattice pattern as described may be further defined by various parameters including, for example, the number of strands (e.g., ribbons), the width of each ribbon/strand, the braiding PPI, and/or the diameter of the forming device (e.g., mandrel diameter), to name a few. Based on the lattice parameters, a leg length and a ribbon angle may be determined. The leg length may define the length of an aspect of the braiding element. For example, if the braiding element is diamond shaped as illustrated in FIG. 17, the length of one side of the diamond shaped braiding element is the "leg length." A ribbon angle may define the angle created by two intersecting aspects of the braiding element. In the example illustrated in FIG. 17, the ribbon angle is the angle formed between two adjacent sides of the diamond shaped braiding element. Radial spacing of braid elements in a lattice pattern can define the width of a braiding element in radial direction. FIG. 18 illustrates an example of a radial spacing, leg length and ribbon angle of a braid element.

Radial spacing of the lattice may be determined as set forth in Equation 1 as follows:

$$\text{Radial Spacing}=(\pi)^*(\text{forming device diameter})/(\text{\#ribbons}/2) \quad \text{Eq. (1):}$$

The braiding element may be fitted into a vessel based on the radial spacing or the diameter of the vessel. The radial spacing of the lattice may be adjusted based on the diameter of the vessel. For example, if the diameter of the vessel is small, the radial spacing may be adjusted to a smaller dimension while the leg length of the braid elements may be maintained. Also in this example, the ribbon angle may also be adjusted to achieve the adjusted radial spacing. Adjusting the ribbon angle may also alter the spacing of the braid element in the PPI direction.

Figure 19:
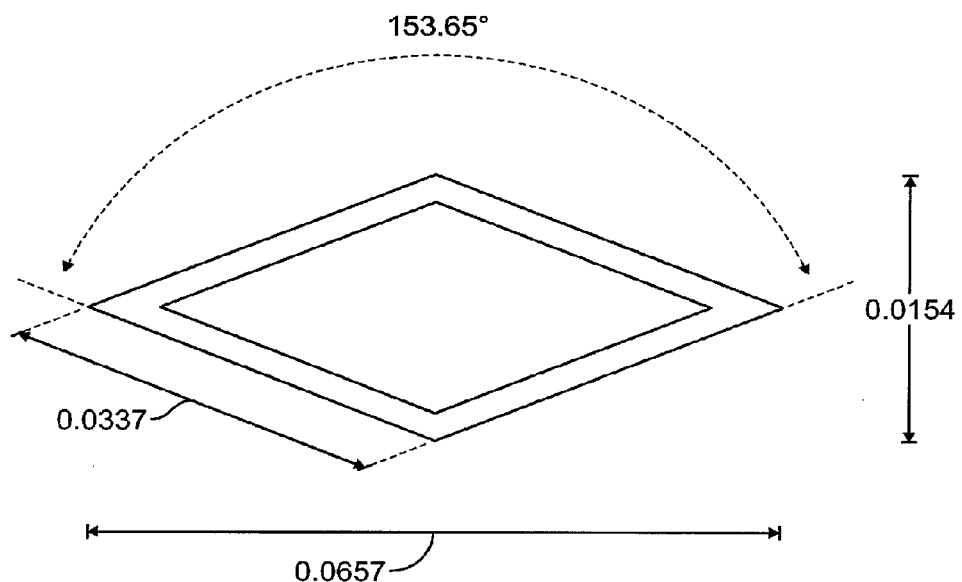
FIG. 19 illustrates an example of another braiding element of a lattice in an occluding device.

FIG. 19 illustrates an example of determining a radial spacing and ribbon angle of a lattice structure in an occluding device. In this example, a lattice or braid contains sixteen interlacing ribbons, with each ribbon being 0.004 inches wide and braided on a forming device such as a mandrel with a diameter of 4.25 mm and 65 PPI. Thus, in this example, the number of braiding elements is sixteen, the ribbon width is 0.004 inches, the spacing in the PPI direction is 1/65=0.01538 inches and the diameter of the forming device (e.g., mandrel diameter) is 4.25 mm. Hence, the radial spacing may be calculated as: Radial spacing=($\pi$)*(forming device diameter)/(#ribbons/2)=(3.14)*(0.425/2.54)/(16/2)=0.0657 inches. FIG. 19 illustrates an example of a braiding element with a radial spacing of 0.0657 inches. In addition, the leg length of the example is 0.0337 inches, the ribbon angle is 153.65 degrees, and the spacing of the braiding element in the PPI direction, based on the ribbon angle and leg length is 0.0154 inches.

Figure 20:
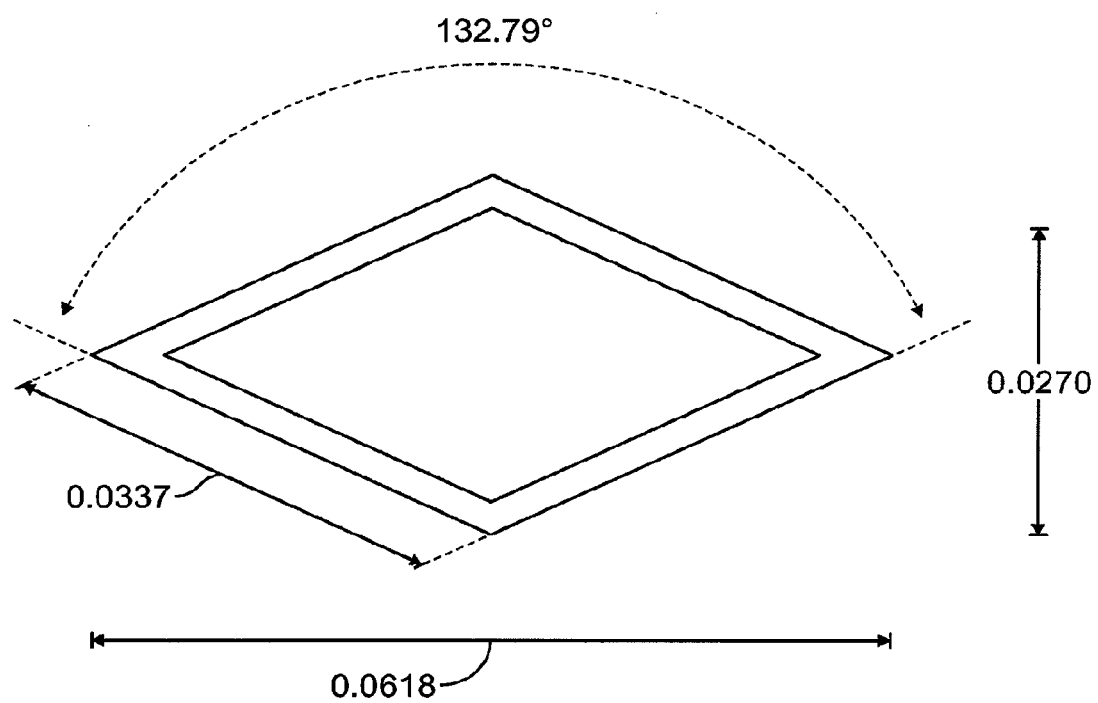
FIG. 20 illustrates a braiding element of an occluding device fitted into a vessel diameter.

FIG. 20 illustrates the example of FIG. 19 after the braiding element is fitted into an appropriate vessel diameter. In this example, the radial spacing is adjusted to a smaller length to accommodate a smaller vessel diameter. The leg length remains constant at 0.0337 inches so the ribbon angle changes based on changes in the radial spacing. In this example, the radial spacing is adjusted to 0.06184 inches and the ribbon angle is adjusted to 132.79 degrees. Also, the spacing of the braid element in the PPI direction is also changed. In this example, the spacing of the braid element in the PPI direction increases from 0.0154 inches to 0.0270 inches.

Table 1 illustrates additional examples of lattice or braid patterns of varying PPI, ribbon width (RW), or number of ribbons. In addition, each of the braid patterns in Table 1 may produce patterns with the same percent coverage within a vessel.

TABLE 1

| # ribbons | 16 | 32 | 64 |
|---|---|---|---|
| Braid diameter (mm) | 4.25 | 4.25 | 4.25 |
| Braid diameter (in) | 0.16732 | 0.16732 | 0.16732 |
| PPI | 65.00 | 130.00 | 260.00 |
| RW (mils) | 4.0000 | 2.0000 | 1.0000 |
| Node Spacing (ppi) | 0.01538 | 0.00769 | 0.00385 |
| Node Spacing (radial) | 0.06571 | 0.03285 | 0.01643 |
| Ribbon Angle (ppi) | 153.65 | 153.65 | 153.62 |
| Leg Length (in) | 0.03374 | 0.01687 | 0.00844 |
| Vessel diameter (mm) | 4 | 4 | 4 |
| In-vessel device Node spacing | 0.06184 | 0.03092 | 0.01546 |
| In-vessel device Ribbon Angle (ppi) | 132.79 | 132.79 | 132.70 |
| In-vessel device Node spacing (ppi) | 0.02702 | 0.01351 | 0.00677 |
| In-vessel device PPI | 37.01 | 74.04 | 147.72 |
| In-vessel device braided closed area (in2) | 0.00024814 | 0.00006203 | 0.00001551 |
| In-vessel device Braided Open Area (in2) | 0.00058741 | 0.00014680 | 0.00003681 |

TABLE 1-continued

| # ribbons | 16 | 32 | 64 |
|---|---|---|---|
| In-vessel device coverage | 29.7% | 29.7% | 29.64% |
| In-vessel device total area (in2) | 0.00083555 | 0.00020883 | 0.00005232 |
| In-vessel device cell size (mm) | 1.317 | 0.658 | 0.329 |

The occluding device may be placed into a protective coil to enhance placement of the occluding device in a vessel. Also, the occluding device may be housed in a delivery device, such as a catheter, for placement within a vessel. The occluding device may be created at a size or dimension based on the size of the protective coil, delivery device, or catheter housing the occluding device. For example, the number of strands or ribbons in the lattice structure of the occluding device that fit into a corresponding protective coil, delivery device, or catheter may be determined such that the occluding device is effectively stored or housed prior to deployment in a vessel. In one example, the strands of the occluding device may overlap in a 2-layer structure including an inner layer and an outer layer, the outer layer contacting the protective coil.

In one example, a housing such as a protective coil, delivery device or catheter that houses the occluding device may have a constant size or diameter and the characteristics of the occluding device may be determined to fit the housing. For example, a ribbon size or width may be determined based on the desired size of the housing. In this way, the size (or diameter) of the housing (e.g., protective coil, delivery device or catheter) may be constant for a variety of occluding devices that may vary in size or number of ribbons.

Figure 21:
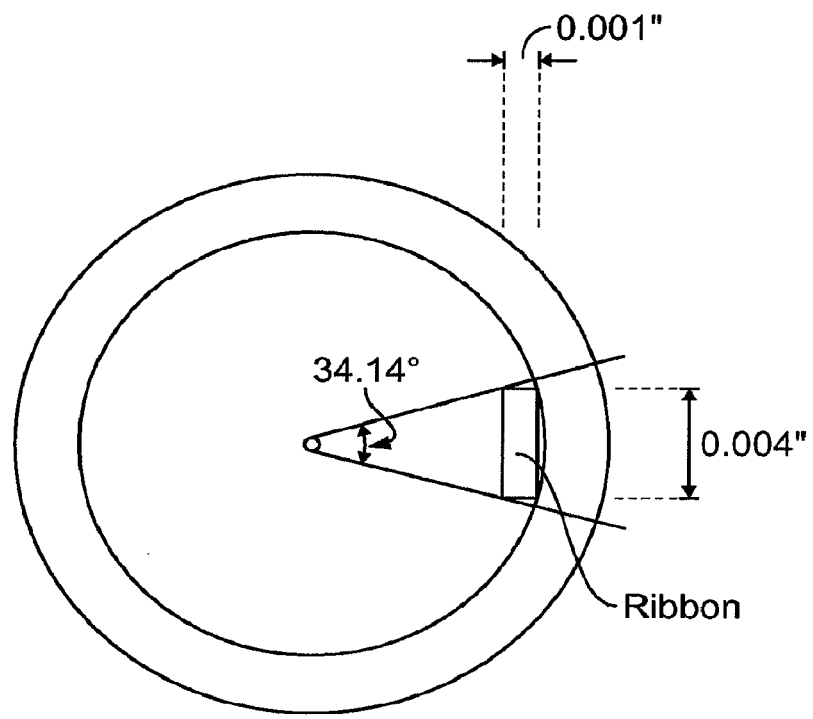
FIG. 21 is a cross sectional view of an example of a protective coil.

FIG. 21 illustrates an example of a cross sectional view of a protective coil. In this example, a number of strands or ribbons in a lattice structure of an occluding device is determined for a protective coil. The protective coil illustrated in FIG. 21 has a circular cross sectional area with a diameter. A strand or ribbon of a predetermined thickness or size is placed within the protective coil such that the outer surface of the strand/ribbon contact the inner surface of the protective coil. The inner surface of the strand/ribbon creates a concave surface within the protective coil. A second strand/ribbon is placed within the protective coil such that the outer surface of the second strand/ribbon contacts an inner circumference in contact with the concave surface of the strand/ribbon previously placed in the protective coil. The angle from a center point of the circular protective coil from one edge of the second strand/ribbon to an opposite edge of the second strand/ribbon is determined (i.e., the "arc-angle"). Based on these measurements, the number of strands or ribbons of the predetermined size or thickness may be determined as follows: (Arc-angle)*(# ribbons/2)<=360 degrees (i.e., # ribbons<=720 degrees/angle).

In the example illustrated in FIG. 21, an occluding device is constructed using a 0.001 by 0.004 inch ribbon. The arc-angle of the ribbon element at the center of the protective coil between a first line drawn from the center point of the protective coil to one edge of an inner layer ribbon and a second line drawn from the center point of the protective coil to the opposite edge of the inner layer ribbon is 34.14 degrees. Thus, the calculated number of ribbons is less than or equal to 720 degrees/34.14 degrees=20 ribbons.

Table 2 illustrates additional examples of different designs for loading a lattice structure of an occluding device in a protective coil.

TABLE 2

| # ribbons | 16 | 32 | 64 |
|---|---|---|---|
| Protective Coil ID (in) | 0.017 | 0.017 | 0.017 |
| Ribbon Width (in) | 0.004 | 0.002 | 0.001 |
| Ribbon Thickness (in) | 0.001 | 0.001 | 0.001 |
| Inner Circle Angle | 36.98 | 17.83 | 8.84 |
| Max # Ribbons fitting in inner circle | 9.73 | 20.19 | 40.72 |
| # ribbons in inner circle | 8 | 16 | 32 |

Figure 22:
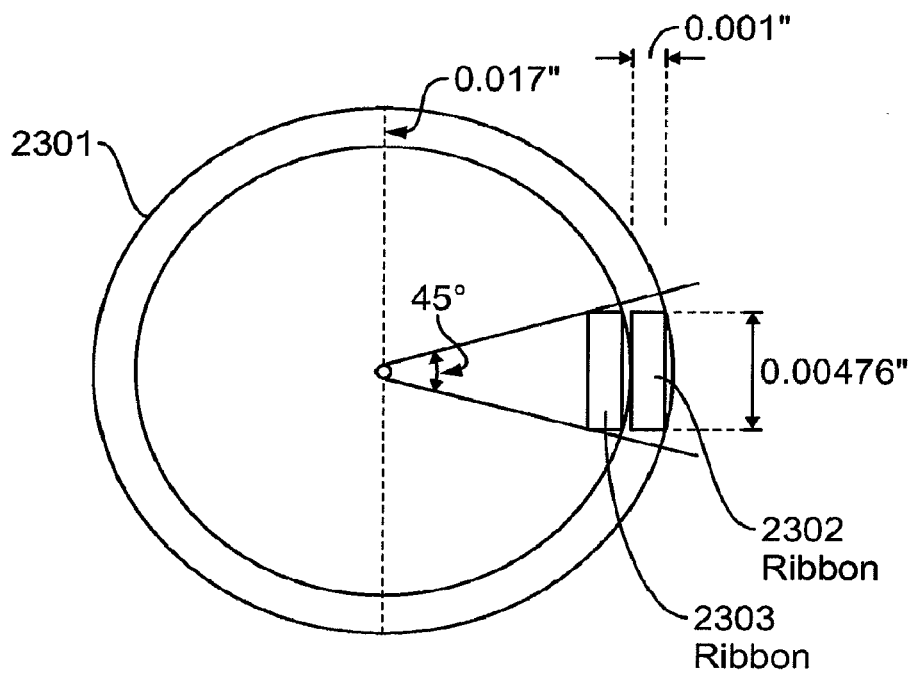
FIG. 22 illustrates an example of determining ribbon dimensions of an occluding device in a protective coil or a delivery device.

FIG. 22 illustrates another example of determining ribbon dimensions for an occluding device in a protective coil or a delivery device. In this example, an occluding device with a lattice or braid structure based on a thickness of a ribbon. As FIG. 22 illustrates, the diameter of the protective coil or delivery device 2301 is 0.0170 inches. A first ribbon 2302 is fitted within the outer surface of the protective coil or delivery device 2301. A second ribbon 2303 is placed in contact with an inner circumference of the protective coil or delivery device 2301 where the inner circumference is a circumference that is tangential to the inner surface of the first ribbon 2302. The second ribbon 2303 is placed within the inner circumference such that lateral ends of the second ribbon 2303 are in contact with the inner circumference of the protective coil or delivery device 2301. The arc-angle between a first line extending from the center point of the protective coil or delivery device 2301 to one lateral end of the second ribbon 2303 and a second line extending from the center point of the protective coil or delivery device 2301 to the other lateral end of the second ribbon 2303 is calculated as illustrated in FIG. 22.

In this example, the maximum dimensions of the first and second ribbons 2302, 2303 are determined based on the calculated arc-angle formed. For example, to allow eight ribbons in the inner circumference of the protective coil or delivery device 2301, the arc-angle may be calculated as (360 degrees)/8=45 degrees as FIG. 22 illustrates. Based on a 45 degree angle, the maximum ribbon width may be determined as 0.00476 inches to allow eight ribbons of a thickness of 0.001 inches to fit within the inner circumference of the protective coil or delivery device 2301.

Figure 23:
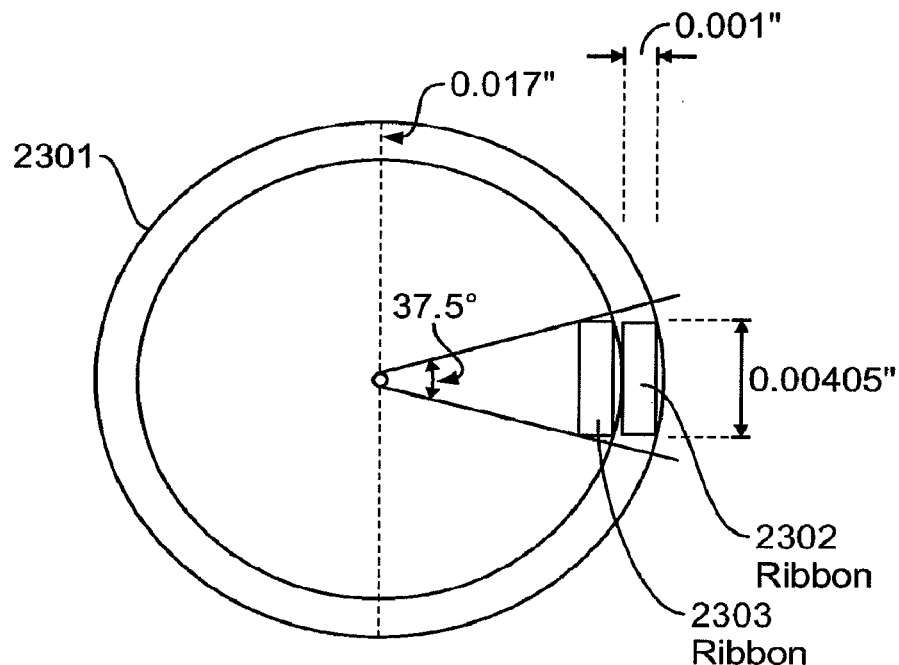
FIG. 23 illustrates another example of determining ribbon dimensions of an occluding device in a protective coil or a delivery device.

In another example, a narrower ribbon width is used to compensate for material tolerance variations and curvature. Based on extensive research and experimentation by the applicants, it was discovered that a tolerance range applied to the ribbon widths of about 20% can compensate for such material tolerance variations. FIG. 23 illustrates an example of a 20% tolerance range or cushion applied to ribbon widths of an occluding device.

In this example, 20% additional ribbons are desired in the occluding device (i.e., 1.20*8=9.6 ribbons). The maximum width of the ribbons may be determined based on the desired number of 9.6 ribbons by calculating the angle as described above. Specifically, the arc-angle may be calculated as (360 degrees)/9.6=37.7 degrees. Based on this calculation, the maximum width of the ribbons may be determined as 0.00405 inches as illustrated in FIG. 23. Thus, in this example, a 20% cushion is applied to permit 9.6 ribbons in the protective coil or delivery device at a maximum width of 0.00405 inches.

Table 3 provides additional examples of ribbon widths for various ribbon thicknesses. In the examples provided in Table 3, the ribbon thicknesses range from 0.0007 inches to 0.0015 inches.

TABLE 3

| Ribbon Thickness (in) | Calculated max width (in) | 20% cushion width (in) |
|---|---|---|
| 0.0005 | 0.00543 | 0.000463 |
| 0.0006 | 0.00530 | 0.00452 |
| 0.0007 | 0.00516 | 0.00440 |
| 0.0008 | 0.00503 | 0.00428 |
| 0.0009 | 0.00490 | 0.00417 |
| 0.0010 | 0.00476 | 0.00405 |
| 0.0011 | 0.00463 | 0.00393 |
| 0.0012 | 0.00450 | 0.00382 |
| 0.0013 | 0.00436 | 0.00370 |
| 0.0014 | 0.00422 | 0.00358 |
| 0.0015 | 0.00409 | 0.00346 |

Figure 24:
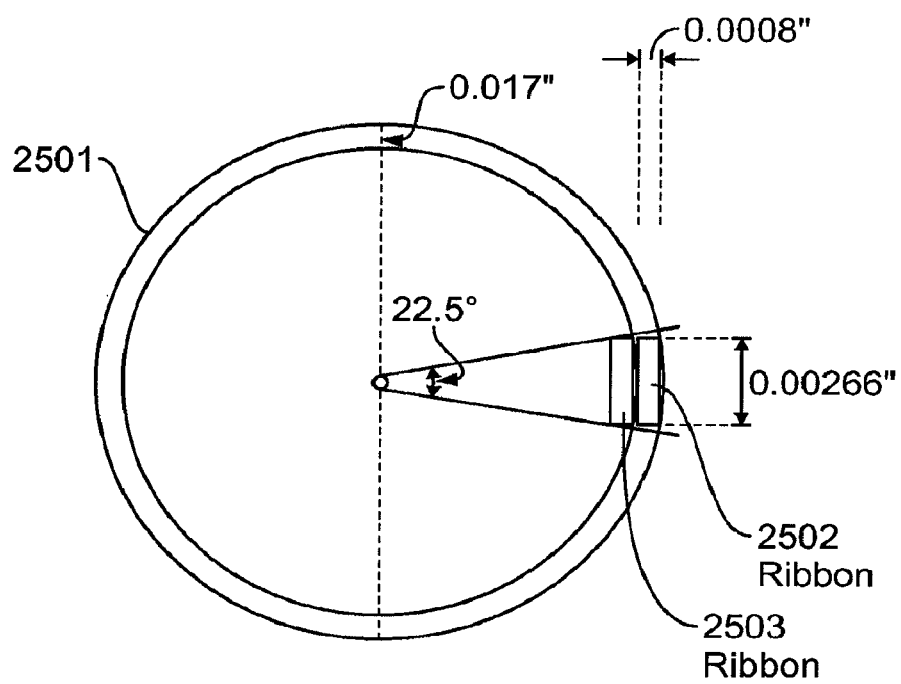
FIG. 24 illustrates an example of determining a ribbon width based on a number of ribbons.

In another example, an occluding device containing 32 ribbons is described. FIG. 24 illustrates an example of determining the ribbon width of a 32-ribbon occluding device based on the number of ribbons that can fit in the protective coil or delivery device 2501. In this example, the protective coil or delivery device 2501 has a diameter of 0.017 inches and the maximum ribbon width that can fit in the inner circumference of the protective coil or delivery device 2501 provides an arc-angle of (360 degrees)/(32/2)=22.5 degrees as illustrated in FIG. 24. Hence, to fit 16 ribbons along the inner circumference of the protective coil 2501, the width of the ribbons is determined to be 0.00266 inches, with a thickness of 0.00080 inches as illustrated in FIG. 24. Similarly a 20% cushion may be applied to the ribbon width to provide for narrower ribbon widths to compensate for material tolerance variations. In this example, the modified ribbon widths may be determined based on the new arc-angle requirement of (360 degrees)/19.2=18.75 degrees. Table 4 provides maximum ribbon widths for a 32-ribbon occluding device.

TABLE 4

| Ribbon Thickness (in) | Calculated max width (in) | 20% cushion width (in) |
|---|---|---|
| 0.0005 | 0.00288 | 0.00242 |
| 0.0006 | 0.00281 | 0.00235 |
| 0.0007 | 0.00273 | 0.00229 |
| 0.0008 | 0.00266 | 0.00223 |
| 0.009 | 0.00258 | 0.00216 |
| 0.0010 | 0.00251 | 0.00210 |

Alternatively, a larger number of ribbons may be included in the occluding device. For example, the strands or ribbons may be increased to greater than 32, such as 40, 44, 48, 50, 56, 60, 64, 70, 76, 80, 90, 100, or more. For any desired number of ribbons, a ribbon width may be determined based on a calculated angle or a ribbon thickness as described. In addition, a cushion may be applied to the ribbon width as described.

Figure 25:
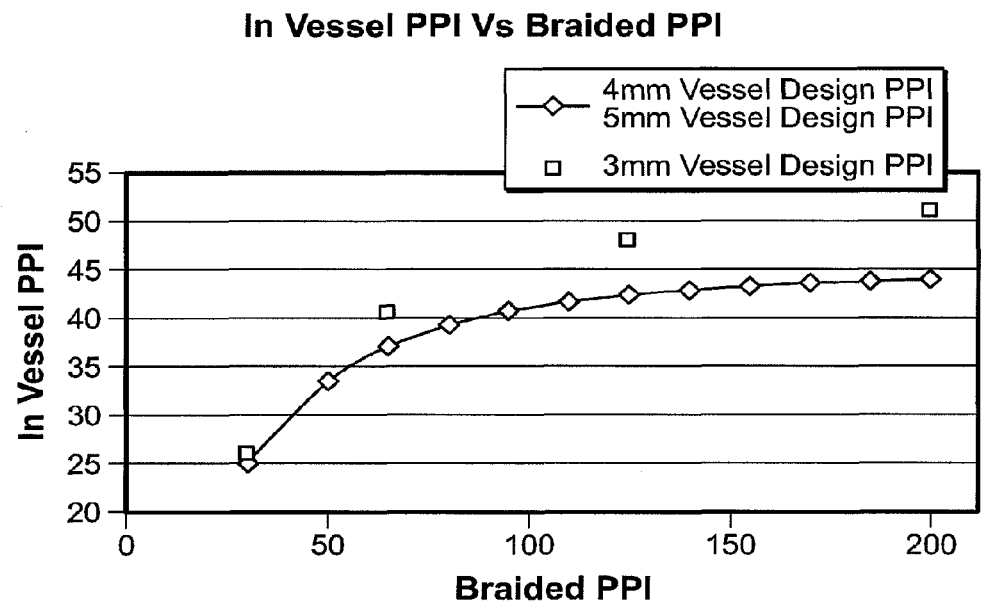
FIG. 25 illustrates a relationship between the PPI of the occluding device in a vessel versus the PPI of the occluding device in a free-standing state.

In another example, oversized occluding devices may be used relative to the vessel. For example, a larger occluding device relative to the size of the vessel lumen may result in enhanced anchoring of the occluding device within the lumen of the vessel. FIG. 25 illustrates a relationship between the PPI of the occluding device in place in the vessel ("in-vessel PPI") versus the PPI of the occluding device in the free-standing state ("braided PPI"). The graph in FIG. 25 demonstrates that for each design, the PPI of the occluding device in place in the vessel approaches a maximum value as the pick count of the occluding device in the free-standing state increases. For example, for the 4 mm vessel design, as the PPI of the free-standing occluding device is increased, the PPI of the occluding device in the vessel increases until the in-vessel PPI reaches about 45. When the in-vessel PPI reaches about 45, further increases in the braided PPI result in only minimal further increases in the in-vessel PPI. Also illustrated in FIG. 25, different vessel designs (e.g., a 3 mm vessel design or 5 mm vessel design) result in a similar behavior in which the in-vessel PPI approaches a maximum value for high braided pick counts.

Figure 28:
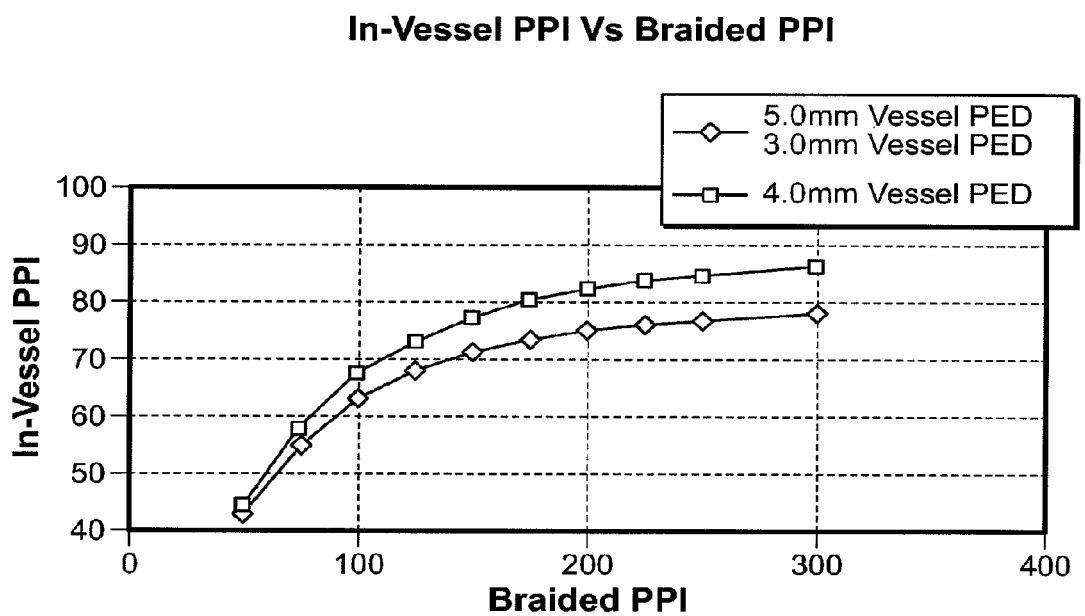
FIG. 28 illustrates the in-vessel PPI as a function of the braided PPI of a 32 ribbon occluding device.

Similarly, FIG. 28 illustrates the in-vessel PPI as a function of the braided PPI of a 32 ribbon occluding device. In the examples illustrated in FIG. 28, the PPI of the occluding device in a vessel ("in-vessel PPI") approaches a maximum value as the PPI of the occluding device in a free-standing state ("braided PPI"). FIG. 28 also illustrates alternate vessel designs. As can be seen in the examples of vessel designs of FIG. 28, for each of the vessel designs, the in-vessel PPI approaches a maximum value asymptotically as the braided PPI increases.

Figure 26:
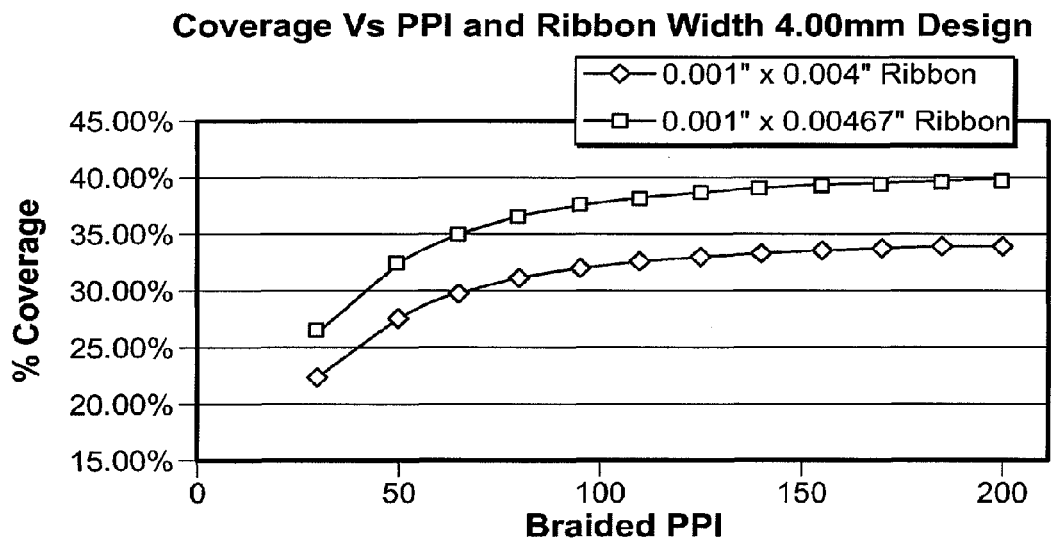
FIG. 26 illustrates an example of a maximum ribbon size that fits in a protective coil.

Similarly, the coverage of the occluding device may be based on ribbon width or braided PPI. FIG. 26 illustrates an example in which the ribbon is 0.00467 inches wide and 0.001 inches and is the maximum ribbon size that fits in the protective coil. As FIG. 26 illustrates, the coverage approaches a maximum value of approximately 65-100 PPI range. In this example, the percentage of coverage asymptotically approaches approximately 40% for a 0.001"×0.00467" ribbon and 34% for a 0.001"×0.004" ribbon.

Figure 29:
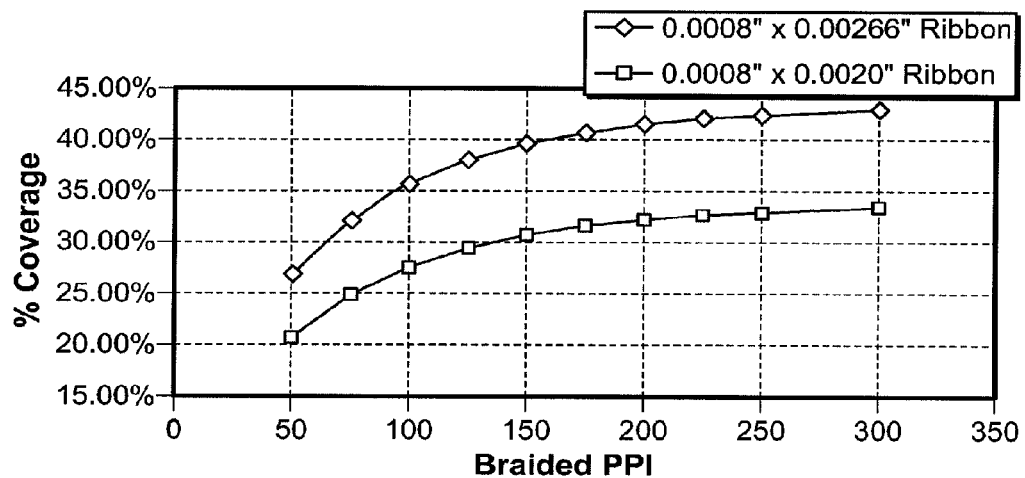
FIG. 29 illustrates the percent coverage as a function of the braided PPI for a 32 ribbon occluding device.

FIG. 29 illustrates the percent coverage as a function of the braided PPI for a 32 ribbon occluding device. As FIG. 29 demonstrates, the % coverage approaches a maximum value as the braided PPI in increases. For example, for an occluding device containing 0.0008×0.00266 inch ribbons, the % coverage approaches a maximum value of about 43% as the braided PPI increases above about 150. Also, for an occluding device containing 0.0008×0.0020 inch ribbons, the % coverage approaches a maximum value of about 35% as the braided PPI increases above about 150.

Figure 27:
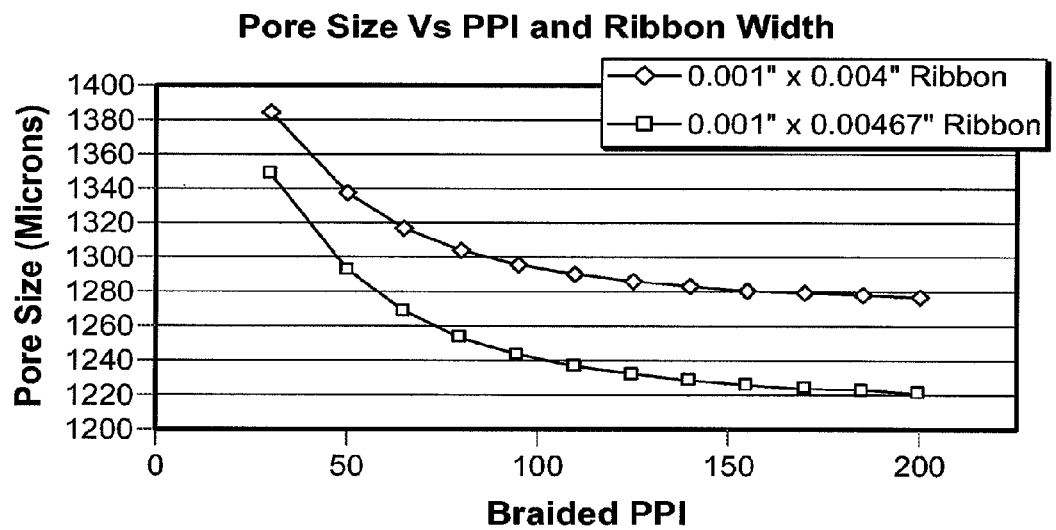
FIG. 27 is a graph showing the opening sizes of braiding elements in the occluding device as a function of the PPI of the lattice structure.

FIG. 27 is a graph showing the opening sizes of braiding elements in the occluding device as a function of the PPI of the lattice structure. As the PPI increases, the opening sizes or spaces through which flow of fluid (e.g., blood) decreases. As the PPI of the lattice structure reaches about 100, the opening sizes of the braiding elements when in place in a vessel asymptotically approaches a minimum value. In the examples illustrated in FIG. 27, for a ribbon size of 0.001×0.004 inches, the opening sizes of the braiding elements in the lattice structure of an occluding device in a vessel approaches 1280 microns or less. Similarly, for a ribbon size of 0.001×0.00467 inches, the opening sizes of the braiding elements in the lattice structure of an occluding device in a vessel approaches about 1220.

Figure 30:
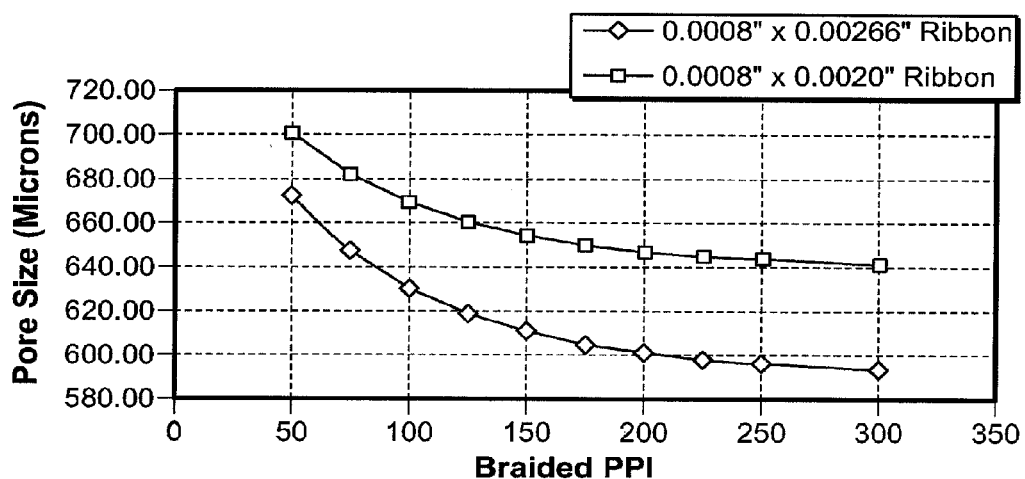
FIG. 30 illustrates the opening sizes of braiding elements in the occluding device as a function of the braided PPI of the lattice structure for a 32 ribbon occluding device.

FIG. 30 illustrates the opening sizes of braiding elements in the occluding device as a function of the braided PPI of the lattice structure for a 32 ribbon occluding device. As FIG. 30 demonstrates, the opening size of braiding elements approaches a minimum value as the braided PPI in increases. For example, for an occluding device containing 0.0008× 0.00266 inch ribbons, the opening size approaches a minimum value of about less than 600 microns as the braided PPI increases above about 150. Also, for an occluding device containing 0.0008×0.0020 inch ribbons, the opening sizes approaches a minimum value of about 640 as the braided PPI increases above about 150.

The occluding device 30 is radially compressible and radially expandable without the need for supplemental radially expanding force, such as an inflatable balloon. The occluding device 30 is constructed by winding the two strands (31, 32 in opposite directions. Alternatively, greater than 2 strands may be wound in various directions. For example, 8, 10, 12, 14, 22, 28, 30, 32, 36, 40, 44, 48, 52, 58, 64, 70, 86, 90, 110, 116, 120, 128, 136, 150, or greater strands may be wound in various directions. In an embodiment, the strands 31, 32 are in the shape of rectangular ribbon (See FIG. 4C). The ribbons can be formed of known flexible materials including shape memory materials, such as Nitinol, platinum and stainless steel.

Figure 4C:
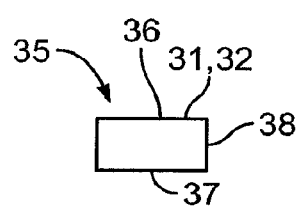
Figure 7:
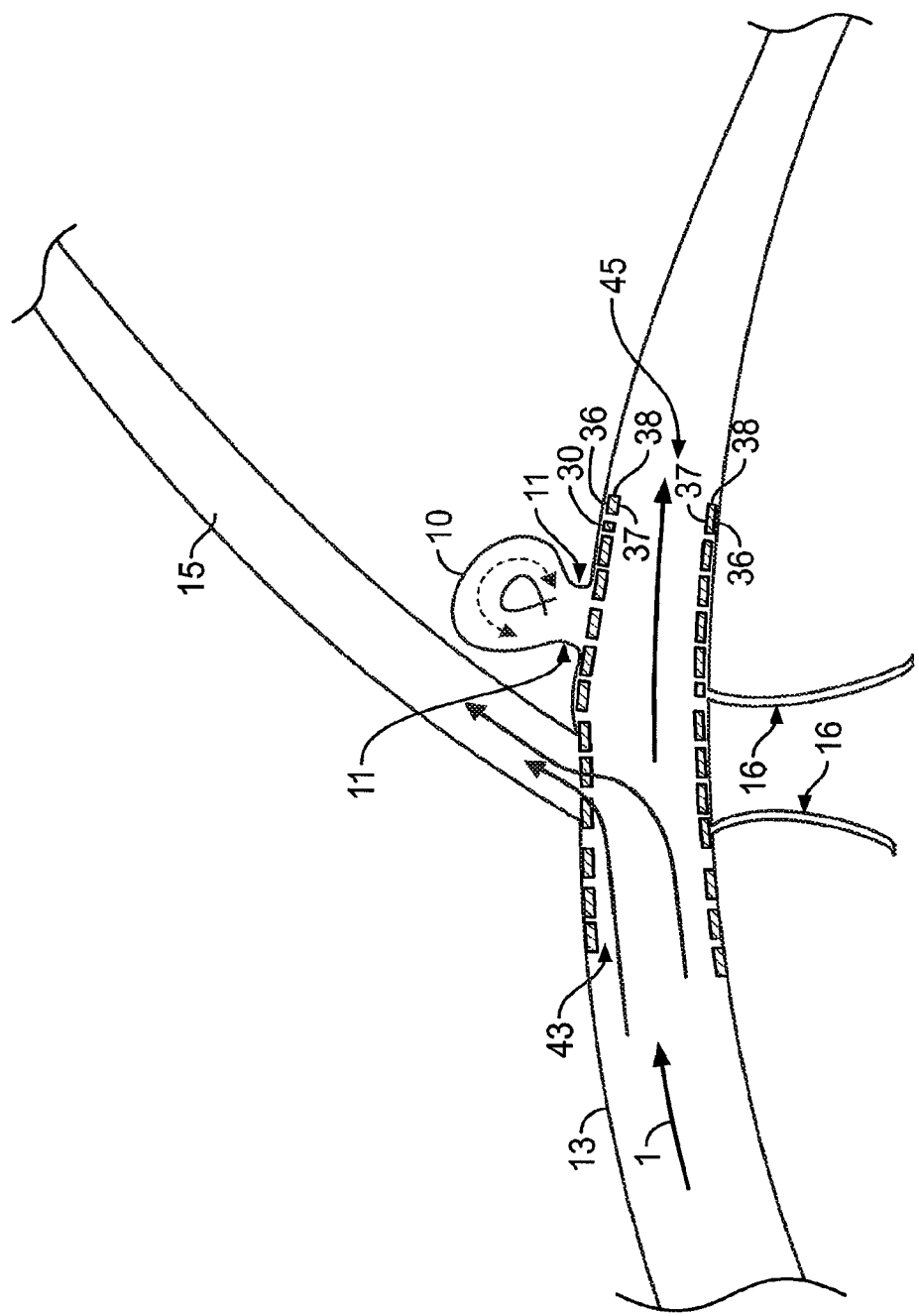
FIG. 7 shows the deployed occluding device inside the lumen of a vessel spanning the neck of the aneurysm, a bifurcation and branch vessels.

The ribbon used as the braiding material for the strands 31, 32 can include a rectangular cross section 35 (FIG. 4C). As shown in FIGS. 4C and 7, the surface 36 that engages an inner surface of the vessel has a longer dimension (width) when compared to the wall 38 that extends between the surfaces 36, 37 (thickness). A ribbon with rectangular cross section has a higher recovery (expansive) force for the same wall thickness when compared to a wire with a circular (round) cross section. Additionally, a flat ribbon allows for more compact compression of the occluding device 20 and causes less trauma to the vascular wall when deployed because it distributes the radial expansion forces over a greater surface area. Similarly, flat ribbons form a more flexible device for a given lattice density because their surface area (width) is greater for a given thickness in comparison to round wire devices.

While the illustrated embodiment discloses a ribbon having a rectangular cross section in which the length is greater than its thickness, the ribbon for an alternative embodiment of the disclosed occluding devices may include a square cross section. In another alternative embodiment, a first portion of the ribbon may include a first form of rectangular cross section and a second portion 39 of the ribbon (FIG. 4B) may include a round, elliptical, oval or alternative form of rectangular cross section. For example, end sections of the ribbons may have substantially circular or oval cross section and the middle section of the ribbons could have a rectangular cross section.

In an alternative embodiment as described above, the occluding device 30 can be formed by winding more than two strands of ribbon. In an embodiment, the occluding device 30 could include as many as sixteen strands of ribbon. In another embodiment, the occluding device 30 can include as many as 32 strands of ribbon, as many as 48 strands of ribbon, as many as 60 strands of ribbon, as many as 80 strands of ribbon, as many as 100 strands of ribbon, as many as 150 strands of ribbon or greater than 150 strands of ribbon, for example. By using standard techniques employed in making radially expanding stents, one can create an occluding device 30 with interstices 34 that are larger than the thickness of the ribbon or diameter of the wire. The ribbons can have different widths. In such an embodiment, the different ribbon(s) can have different width(s) to provide structure support to the occluding device 30 and the vessel wall. The ribbons according to the disclosed embodiments can also be formed of different materials. For example, one or more of the ribbons can be formed of a biocompatible metal material, such as those disclosed herein, and one or more of the ribbons can be formed of a biocompatible polymer.

FIG. 5 shows the intravascular occluding device 30 in a radially compressed state located inside the micro-catheter 25. In one embodiment, the occluding device 30 could be physically attached to the catheter tip. This could be accomplished by constraining the occluding device 30 in the distal segment of the micro-catheter. The micro-catheter 25 is slowly advanced over a guidewire (not shown) by a plunger 50 and when the tip of the micro-catheter 25 reaches the aneurysm, the occluding device is released from the tip. The occluding device 30 expands to the size of the vessel and the surface of the occluding device 30 is now apposed to the vessel wall 15 as shown in FIG. 6. Instruments and methods for delivering and deploying the occluding device 30 are disclosed in the above-referenced copending application.

With reference to FIG. 7, the occluding device 30 is deployed inside the lumen of a cerebral vessel 13 with an aneurysm 10. During its deployment, the proximal end 43 of the occluding device 30 is securely positioned against the lumen wall of the vessel 13 before the bifurcation 15 and the distal end 45 of the occluding device 30 is securely positioned against the lumen wall of the vessel 13 beyond the neck 11 of aneurysm 10. After the occluding device 30 is properly positioned at the desired location within the vessel 13 (for example, see FIG. 7), flow inside the lumen of aneurysm 10 is significantly minimized while the axial flow within the vessel 13 is not significantly compromised, in part due to the minimal thickness of the walls 38.

The flow into the aneurysm 10 will be controlled by the lattice density of the ribbons and the resulting surface coverage. Areas having greater lattice densities will have reduced radial (lateral) flow. Conversely, areas of lesser lattice densities will allow significant radial flow through the occluding device 30. As discussed below, the occluding device 30 can have longitudinally extending (lateral) areas of different densities. In each of these areas, their circumferential densities can be constant or vary. This provides different levels of flow through adjacent lateral areas. The location within a vessel of the areas with greater densities can be identified radiographically so that the relative position of the occluding device 30 to the aneurysm 10 and any vascular branches 15, 16 can be determined. The occluding device 30 can also include radiopaque markers.

Figure 8:
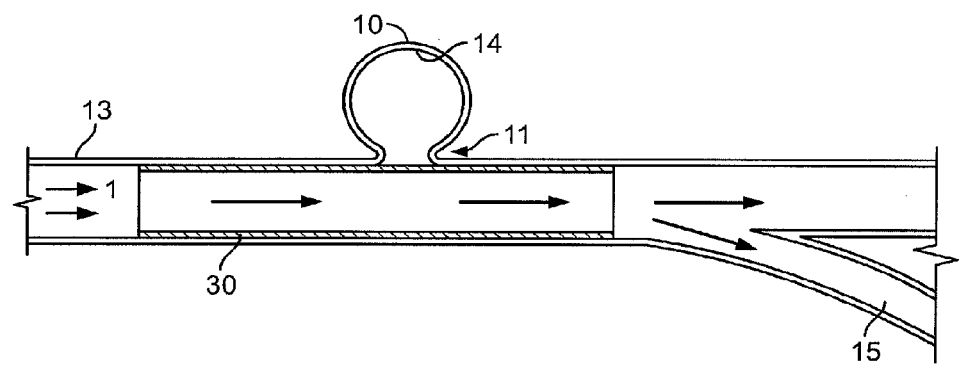
FIG. 8 is a schematic showing the occluding device located in the lumen of a vessel and the change in the direction of the blood flow.

The reduction of blood flow within the aneurysm 10 results in a reduction in force against the wall 14 and a corresponding reduction in the risk of vascular rupturing. When the force and volume of blood entering the aneurysm 10 is reduced by the occluding device, the laminar flow into the aneurysm 10 is stopped and the blood within the aneurysm begins to stagnate. Stagnation of blood, as opposed to continuous flow through the lumen 12 of the aneurysm 10, results in thrombosis in the aneurysm 10. This also protects the aneurysm from rupturing. Additionally, due to the density of the portion of the occluding device 30 at the bifurcation 15, the openings (interstices) 34 in the occluding device 30 allow blood flow to continue to the bifurcation 15 and the side branches 16 of the vessel. If the bifurcation 15 is downstream of the aneurysm, as shown in FIG. 8, the presence of the occluding device 30 still channels the blood away from the aneurysm 10 and into the bifurcation 15.

Figure 9:
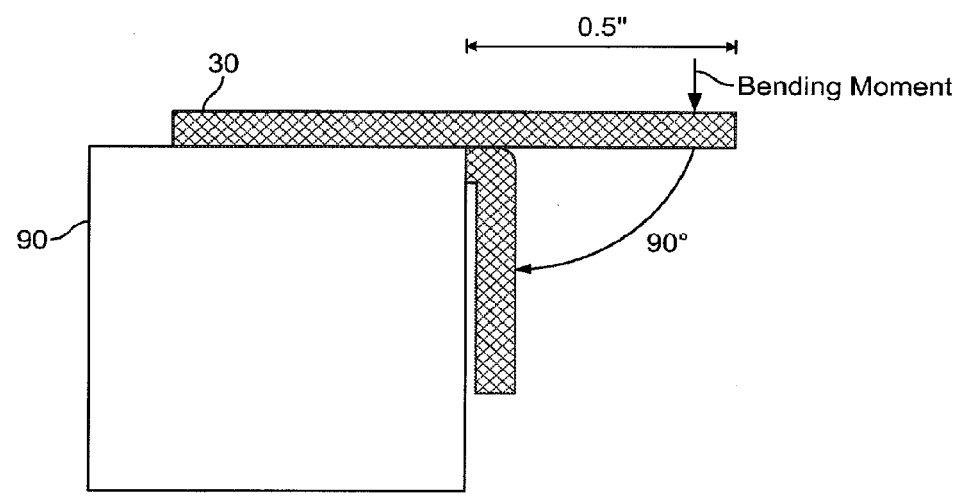
FIG. 9 shows the effect of a bending force on a conventional stent compared to the occluding device of the present invention.

The occluding devices described herein have flexibility to conform to the curvature of the vasculature. This is in contrast to coronary stents that cause the vasculature to conform essentially to their shape. The ability to conform to the shape of the vasculature is more significant for neurovascular occluding devices than coronary stents, as the vasculature in the brain is smaller and more tortuous. Tables 5 and 6 demonstrate these characteristics of the claimed neurovascular occluding device. To demonstrate that the disclosed occluding devices exhibit very desirable bending characteristics, the following experiment was performed. The occluding device made by the inventors was set on a support surface 90 as shown in FIG. 9. About 0.5 inches of the occluding device 30 was left unsupported. Then, a measured amount of force was applied to the unsupported tip until the occluding device was deflected by 90 degrees from the starting point. A similar length of a commercially available coronary stent was subjected to the same bending moment. The results are shown in Table 5. Similar to the reduced compressive force, the occluding device of the present invention required an order of magnitude lower bending moment (0.005 lb-in compared to 0.05 lb-in for a coronary stent).

TABLE 5

Bending Force Required to Bend a 0.5" Cantilever Made by the Occlusion Device

| Coronary stent | commercially available stent | 0.05 lb-in |
|---|---|---|
| Neurovascular | Occluding Device (30) | 0.005 lb-in |

The occluding devices according to the present invention also provides enhanced compressibility (i.e., for a given force how much compression could be achieved or to achieve a desired compression how much force should be exerted) compared to coronary stents. An intravascular device that is not highly compressible is going to exert more force on the vessel wall compared to a highly compressible device. This is of significant clinical impact in the cerebral vasculature as it is detrimental to have an intravascular device that has low compressibility.

TABLE 6

Figure 10:
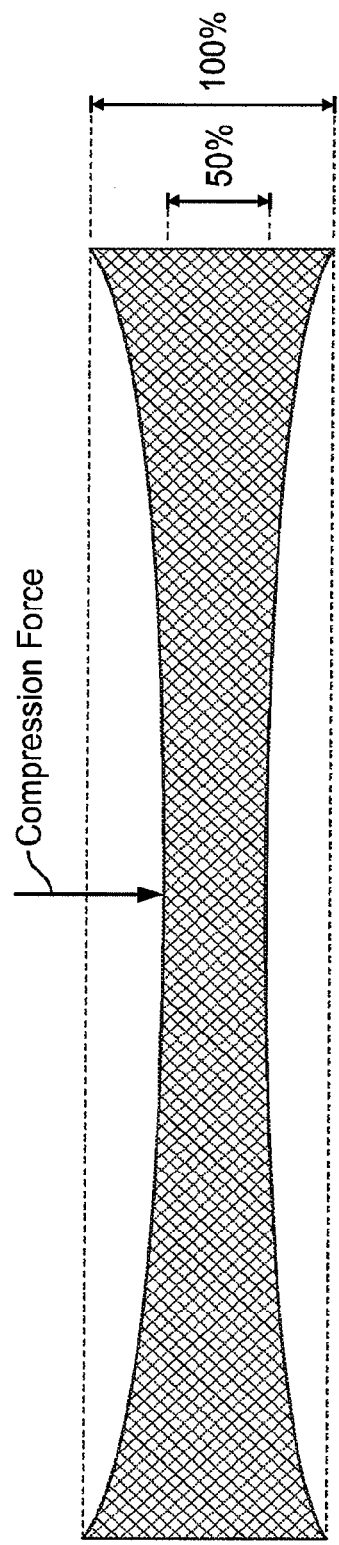
FIG. 10 demonstrates the flexibility of the current invention, compared to a traditional stent, by the extent of the deformation for an applied force.

Compressive Force Required to Compress the Occluding device to 50% of the Original Diameter (See FIG. 10)

| Coronary stent | (commercially available | 0.2 lb |
|---|---|---|
| Neurovascular | Occluding device (30) | 0.02 lb |

Figure 11:
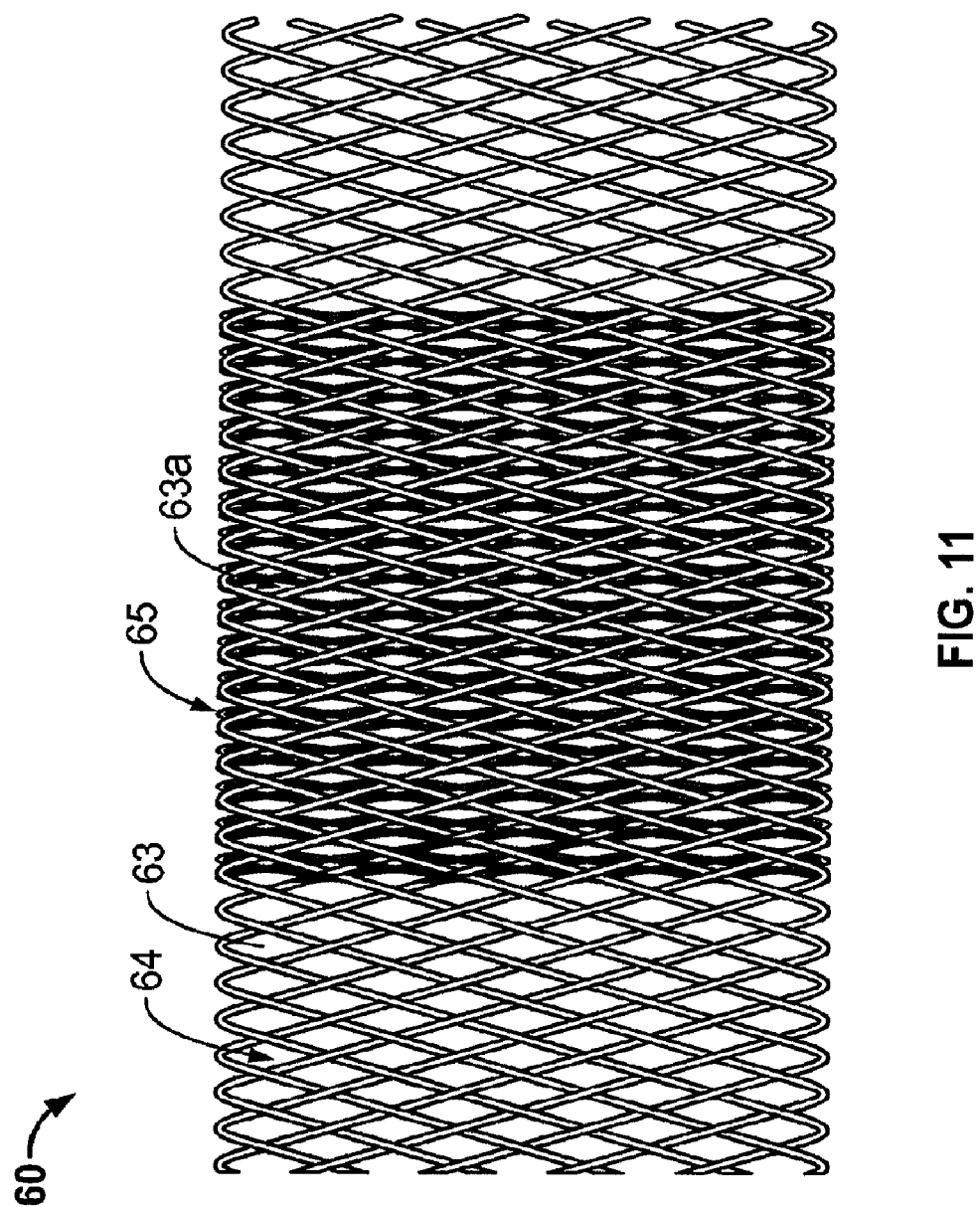
FIG. 11 shows the non-uniform density of the braid that provides the desired curved occluding device.
Figure 12:
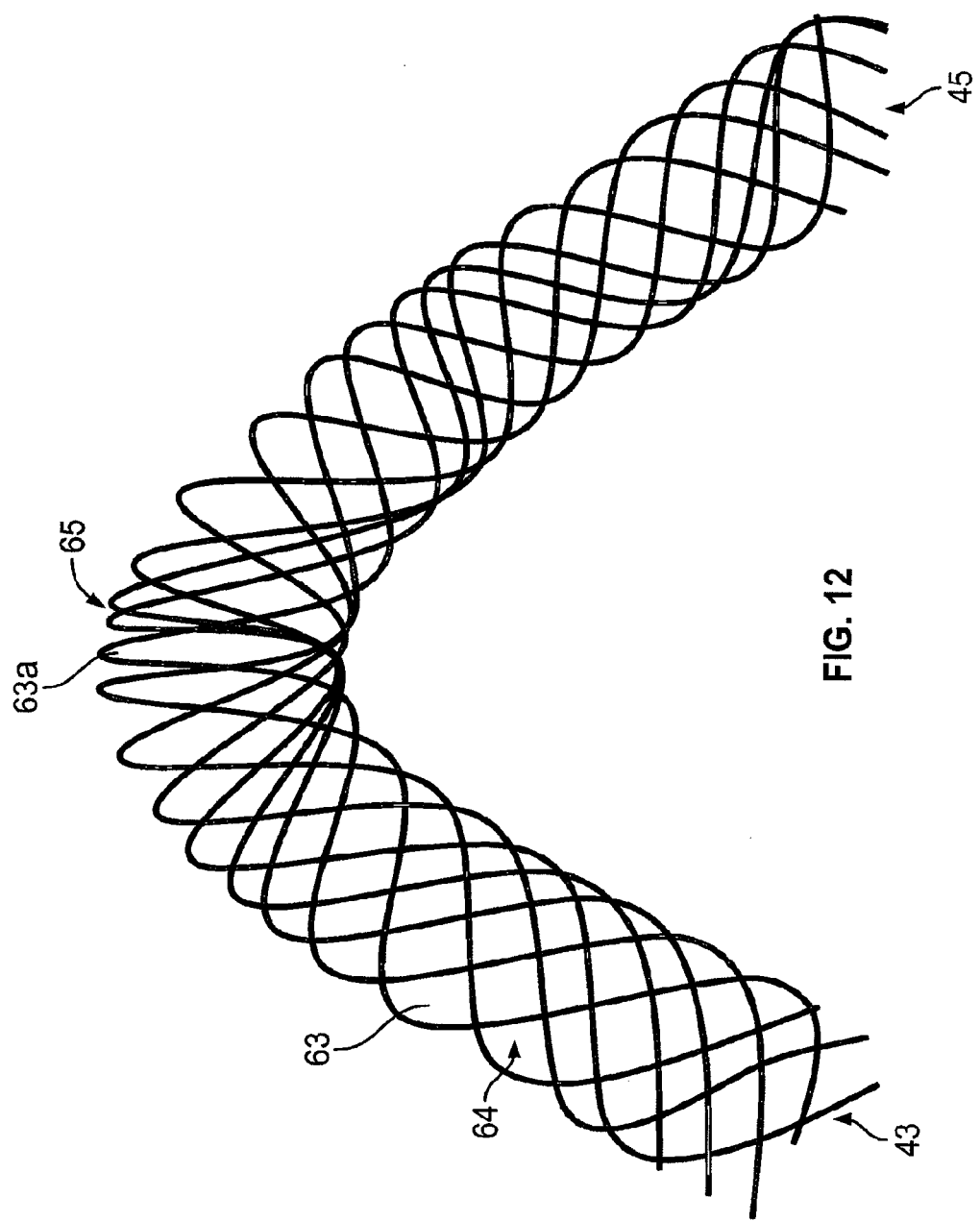
FIG. 12 illustrates the difference in lattice density or porosity due to the non-uniform density of the braiding of the occluding device.
Figure 13:
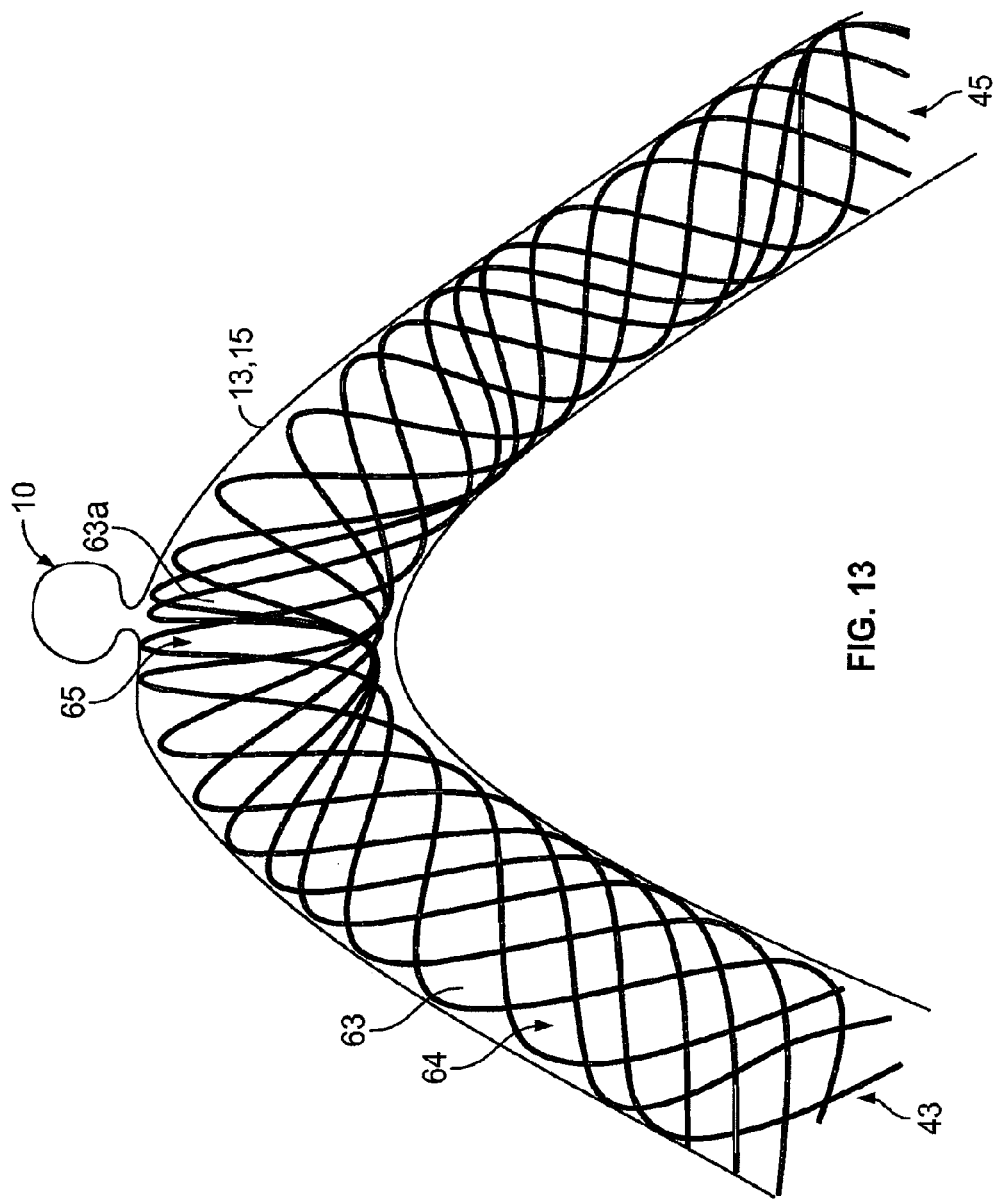
FIG. 13 shows the varying lattice density occluding device covering the neck of an aneurysm.

FIGS. 11-13 show an embodiment of the occluding device 60 in which the lattice structure 63 of the occluding device 60 is non-uniform across the length of the occluding device 60. In the mid-section 65 of the occluding device 60, which is the section likely to be deployed at the neck of the aneurysm, the lattice density 63a is intentionally increased to a value significantly higher than the lattice density elsewhere in the occluding device 60. For example, as seen in FIG. 11, lattice density 63A is significantly higher than the lattice density 63 in adjacent section 64. At one extreme, the lattice density (porosity provided by the interstices) could be zero, i.e., the occluding device 60 is completely impermeable. In another embodiment, the lattice density 63A in mid-section 65 could be about 50%, while the lattice density in the other sections 64 of the occluding device is about 25%. FIG. 12 shows such an occluding device 60 in a curved configuration and FIG. 13 shows this occluding device 60 deployed in the lumen of a vessel. FIG. 13 also illustrates the part of the occluding device 60 with increased lattice density 63A positioned along the neck of aneurysm 10. As with any of the disclosed occluding devices, the lattice density of at least one portion of occluding device 60 can be between about 20% and about 80%. The lattice density of these embodiments could be between about 25% and about 50%.

Figure 14:
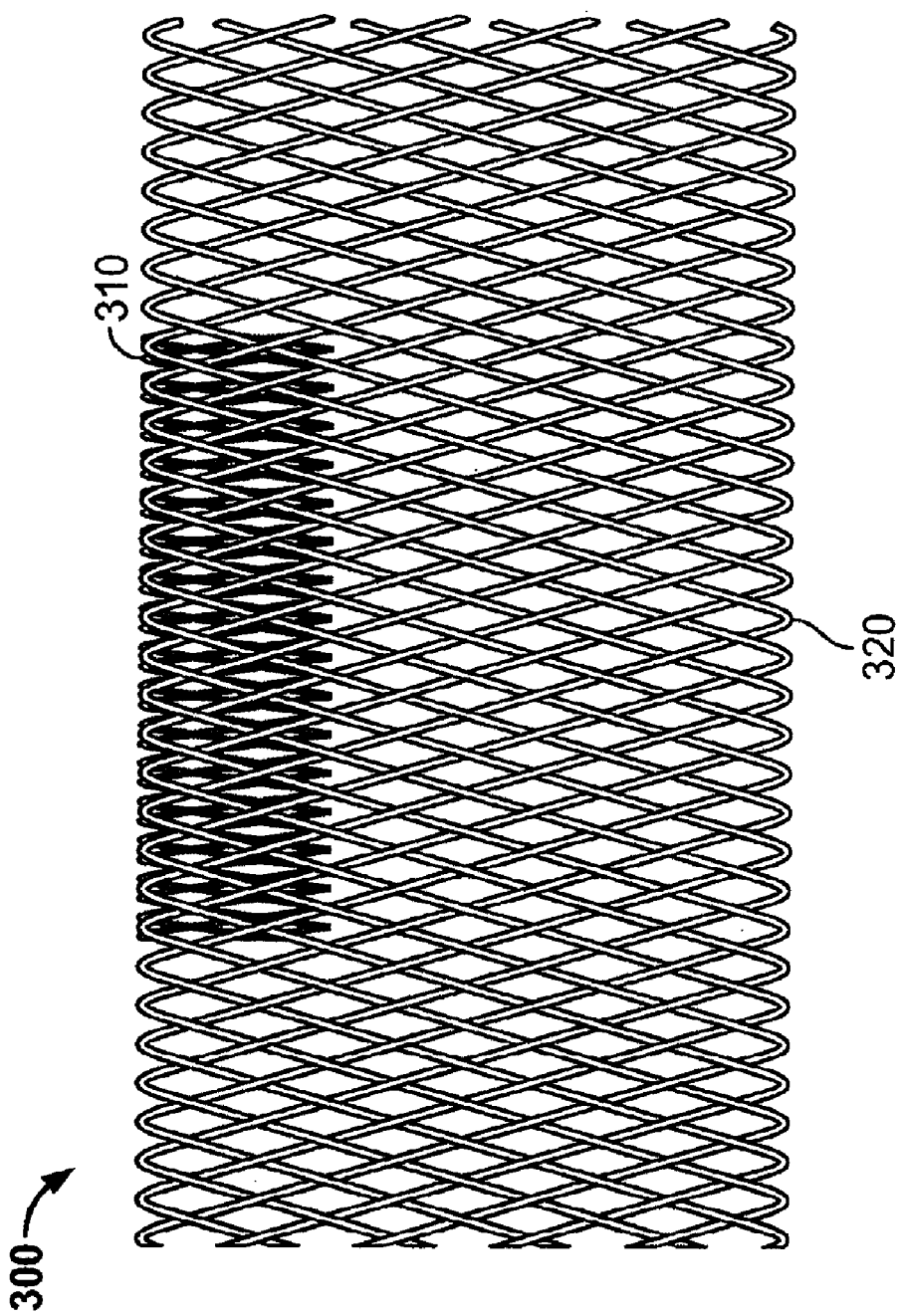
FIGS. 14 and 15 show an embodiment of the vascular occluding device where the lattice density is asymmetrical about the longitudinal axis near the aneurysm neck.
Figure 15:
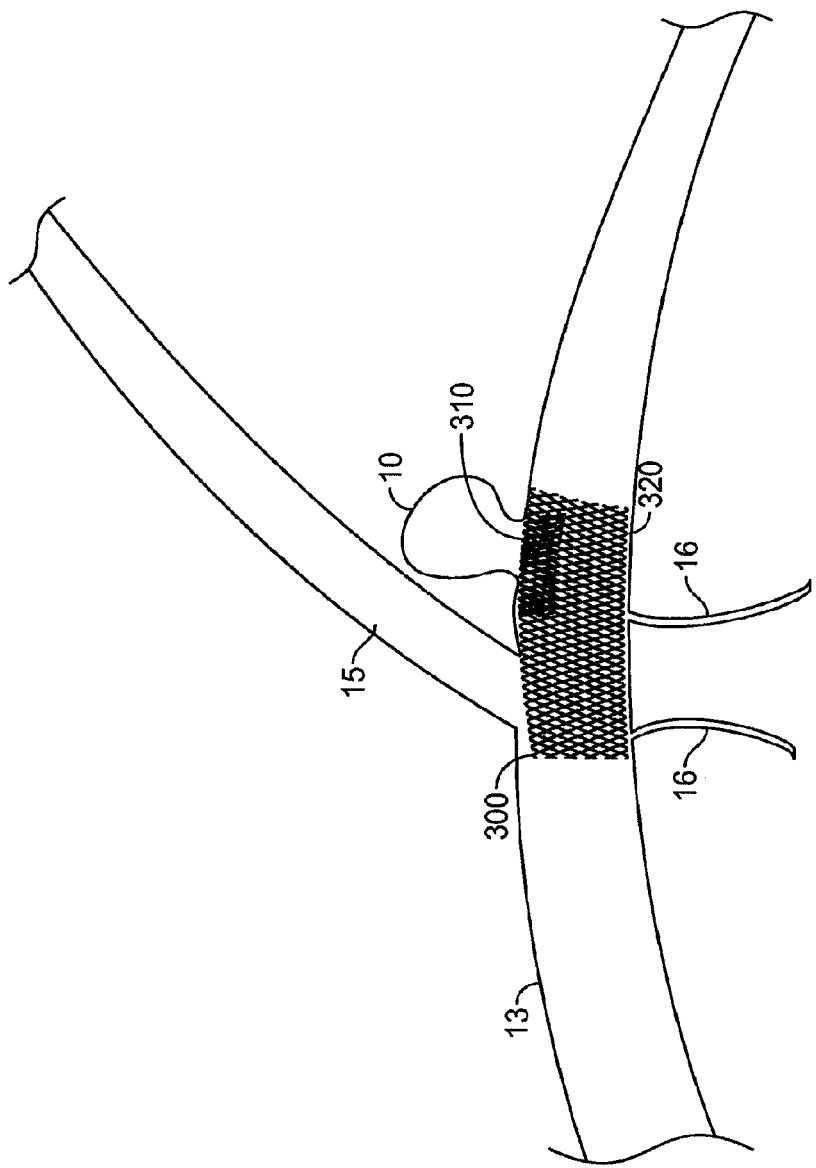

Another embodiment of the occluding device 300 is shown in FIGS. 14 and 15. In this embodiment, the occluding device 300 is deployed in lumen of a vessel with an aneurysm. The occluding device 300 includes a surface 310 that faces the lumen of the aneurysm. This surface 310 has a significantly higher lattice density (smaller and/or fewer interstices) compared to the diametrically opposite surface 320. Due to the higher lattice density of surface 310, less blood flows into the lumen of the aneurysm. However, there is no negative impact on the blood flow to the side branches as the lattice density of the surface 320 facing the side branches is not reduced.

Figure 16:
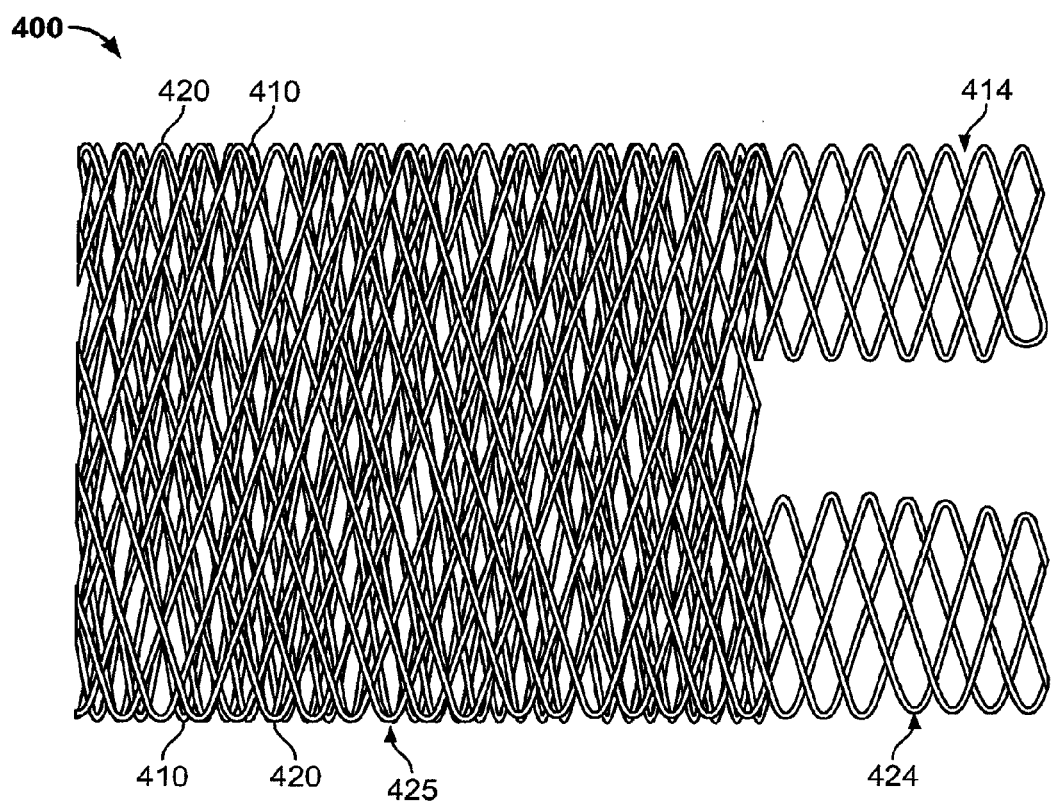
FIG. 16 illustrates a bifurcated occluding device according to an embodiment of the present invention in which two occluding devices of lesser densities are combined to form a single bifurcated device.

Any of the occluding devices disclosed herein can be used with a second occluding device to create a bifurcated occluding device 400 as shown in FIG. 16. This device could be created in vivo. In forming the occluding device 400, a portion of a first occluding device 410 having a low density can be combined with a portion of a second occluding device 410 that also has a low density. The occluding devices 410, 420 can be any of those discussed herein. After these portions of the two occluding devices 410, 420 are combined in an interwoven fashion to form an interwoven region 425, the remaining portions 414, 424 can branch off in different directions, thereby extending along two branches of the bifurcation. Areas outside of the interwoven region 425 can have greater lattice density for treating an aneurysm or lesser lattice density for allowing flow to branches 15, 16 of the vessel.

The density of the lattice for each of the disclosed occluding devices can be about 20% to about 80% of the surface area of its occluding device. In an embodiment, the lattice density can be about 20% to about 50% of the surface area of its occluding device. In yet another embodiment, the lattice density can be about 20% to about 305 of the surface area of its occluding device.

A typical occluding device having sixteen strand braids with 0.005 inch wide ribbon, 30 picks per inch (PPI) (number of crosses/points of contact per inch), and 0.09 inch outer diameter has approximately 30% of lattice density (surface covered by the ribbon). In the embodiments disclosed herein, the ribbon can be about 0.001 inch thick with a width of between about 0.002 inch to about 0.005 inch. In an embodiment, the ribbon has a thickness of about 0.004 inch. For a 16-strands ribbon that is about 0.001 inch thick and about 0.004 inch wide, the coverage for 50 PPI, 40 PPI, and 30 PPI will have 40%, 32% and 24% approximate surface coverage, respectively. For a 16-strands ribbon that is about 0.001 inch thick and about 0.005 inch wide, the coverage for 50 PPI, 40 PPI, and 30 PPI will be about 50%, 40% and 30% approximate surface coverage, respectively.

In choosing a size for the ribbon, one must consider that, when the ribbons are bundled up, will they traverse through a micro-catheter. For example, sixteen strands of a 0.006 inch wide ribbon may not pass through a micro-catheter having an internal diameter of 0.027 inch or less. However, as the width of ribbons become smaller, the recovery strength may decrease proportionally.

While other strand geometry may be used, these other geometries, such as round, will limit the device due to their thickness dimension. For example, a round wire with a 0.002 inch diameter will occupy up to 0.008 inch in cross sectional space within the vessel. This space can impact and disrupt the blood flow through the vessel. The flow in the vessel can be disrupted with this change in diameter.

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as defined in the appended claims. Therefore, the scope of the invention should be determined by the appended claims and their legal equivalents. Furthermore, no element, component or method step is intended to be dedicated to the public regardless of whether the element, component or method step is explicitly recited in the claims.

In the claims, reference to an element in the singular is not intended to mean "one and only one" unless explicitly stated, but rather is meant to mean "one or more." In addition, it is not necessary for a device or method to address every problem that is solvable by different embodiments of the invention in order to be encompassed by the claims.

What is claimed is:

1. A system comprising:
a self-expanding device comprising, in a cross-section, a first layer having strands and a second layer having strands, the strands of the first layer and the strands of the second layer being helically wound in a lattice structure arranged as a flexible tubular body;
wherein the first layer of the self-expanding device comprises a first cross-sectional diameter, wherein each said strand of the first layer is circumferentially spaced from an adjacent said strand of the first layer device by an arc angle calculated by dividing 360 degrees by the number of strands in the first layer, wherein, with respect to a delivery device, each said strand of the first layer comprises a strand cross-sectional dimension being about equal to or less than (a circumference of an inner surface of the delivery device)/(a total number of strands in the first layer); and
wherein the second layer of the device comprises a second cross-sectional diameter different than the first cross-sectional diameter, wherein each said strand of the second layer is circumferentially spaced from an adjacent said strand of the second layer by the arc angle, wherein each said strand of the second layer comprises the strand cross-sectional dimension;
wherein the self-expanding device is configured to have a surface coverage that is less than or equal to 40% when expanded out of the delivery device.

2. The system of claim 1, wherein a total number of strands of the self-expanding device is 32, 48 or 64.

3. The device of claim 1, wherein the self-expanding device comprises a picks-per-inch of 65, 130 or 260.

4. The system of claim 1, wherein the strand cross-sectional dimension has maximum values having a tolerance of 20%.

5. The device of claim 1, wherein the outer first layer of strands contacts an inner surface of the delivery device, and the second layer of strands contacts the first layer.

6. The device of claim 1, further comprising the delivery device.

7. A system comprising:
a self-expanding device comprising, in a cross-section, a first layer having strands and a second layer having strands, the strands of the first layer and the strands of the second layer being helically wound in a lattice structure arranged as a flexible tubular body;
wherein the first layer of the device comprises a first cross-sectional diameter, wherein each said strand of the first layer is circumferentially spaced from an adjacent said strand of the first layer by a first arc angle calculated by dividing 360 degrees by the first number of strands in the first layer, wherein, with respect to a delivery device, each said strand of the first layer comprises a strand cross-sectional dimension being about equal to or less than (a circumference of an inner surface of the delivery device)/(half a total number of strands in the device); and
wherein the first layer of the device comprises a second cross-sectional diameter different than the first cross-sectional diameter, wherein each said strand of the second layer is circumferentially spaced from an adjacent said strand of the second layer by a second arc angle calculated by dividing 360 degrees by the second number of strands in the second layer, wherein each said strand of the second layer comprises the strand cross-sectional dimension;

wherein the self-expanding device is configured to have a surface coverage that is less than or equal to 40% when expanded out of the delivery device.

8. The system of claim 7, wherein the first total number of strands of the device is 32, 48 or 64.

9. The device of claim 7, wherein the device comprises a picks-per-inch of 65, 130 or 260.

10. The system of claim 7, wherein the strand cross-sectional dimension has maximum values having a tolerance of 20%.

11. The device of claim 7, wherein the first layer of strands contacts an inner surface of the delivery device, and the second layer of strands contacts the first layer.

12. The device of claim 7, further comprising the delivery device.

* * * * *